US008507525B2

(12) United States Patent
Guitton et al.

(10) Patent No.: US 8,507,525 B2
(45) Date of Patent: *Aug. 13, 2013

(54) METHODS FOR THE TREATMENT OF TINNITUS INDUCED BY COCHLEAR EXCITOTOXICITY

(75) Inventors: Matthieu Guitton, Le Houlme (FR); Jean-Luc Puel, Coumonterral (FR); Remy Pujol, Montpellier (FR); Jerome Ruel, Montpellier (FR); Jing Wang, Lunel (FR)

(73) Assignee: Auris Medical AG, Lohn-Ammannsegg (CH)

(*) Notice: Subject to any disclaimer, the term of this patent is extended or adjusted under 35 U.S.C. 154(b) by 466 days.

This patent is subject to a terminal disclaimer.

(21) Appl. No.: 12/752,556

(22) Filed: Apr. 1, 2010

(65) Prior Publication Data

US 2010/0254907 A1  Oct. 7, 2010

Related U.S. Application Data

(63) Continuation of application No. 11/236,941, filed on Sep. 28, 2005, now abandoned, which is a continuation-in-part of application No. 10/812,298, filed on Mar. 29, 2004, now Pat. No. 8,268,866.

(51) Int. Cl.
*A61K 31/4704* (2006.01)
*A61K 31/495* (2006.01)

(52) U.S. Cl.
USPC .................. 514/312; 514/252.12; 514/650

(58) Field of Classification Search
USPC ..................... 514/312, 252.12, 650
See application file for complete search history.

(56) References Cited

U.S. PATENT DOCUMENTS

| | | | |
|---|---|---|---|
| 3,254,124 A | 5/1966 | Stevens | |
| 5,421,818 A | 6/1995 | Arenberg | |
| 5,474,529 A | 12/1995 | Arenberg | |
| 5,476,446 A | 12/1995 | Arenburg | |
| 5,654,337 A | 8/1997 | Roentsch et al. | |
| 5,716,961 A | 2/1998 | Sands et al. | |
| 5,770,559 A | 6/1998 | Manning et al. | |
| 5,863,927 A | 1/1999 | Smith et al. | |
| 6,017,961 A | 1/2000 | Flores et al. | |
| 6,045,528 A | 4/2000 | Arenberg et al. | |
| 6,066,852 A | 5/2000 | Zenner et al. | |
| 6,120,484 A | 9/2000 | Silverstein | |
| 6,265,379 B1 | 7/2001 | Donovan | |
| 6,309,410 B1 | 10/2001 | Kuzma et al. | |
| 6,316,428 B1 | 11/2001 | Crandall | |
| 6,377,849 B1 | 4/2002 | Lenarz | |
| 6,638,981 B2 | 5/2003 | Williams et al. | |
| 6,638,081 B2 | 10/2003 | Korsunsky et al. | |
| 6,656,172 B1 | 12/2003 | Hildebrand | |
| 8,268,866 B2* | 9/2012 | Guitton et al. | 514/312 |
| 2002/0068718 A1 | 6/2002 | Pierce | |
| 2002/0082554 A1 | 6/2002 | Lenarz et al. | |
| 2002/0161033 A1 | 10/2002 | Przewosny et al. | |
| 2003/0082214 A1 | 5/2003 | Williams et al. | |
| 2003/0143195 A1 | 7/2003 | Pinsker | |
| 2003/0225116 A1 | 12/2003 | Chizh et al. | |
| 2004/0062819 A1 | 4/2004 | Hildebrand | |

FOREIGN PATENT DOCUMENTS

| | | |
|---|---|---|
| CA | 2548892 | 6/2005 |
| DE | 2062620 | 7/1971 |
| DE | 10124953 | 12/2002 |
| GB | 1330878 | 9/1973 |
| JP | 2001-187737 | 7/2001 |
| WO | WO 9408599 | 4/1994 |
| WO | WO 9738698 | 10/1997 |
| WO | WO 98/10757 A2 | 3/1998 |
| WO | WO 0110833 | 2/2001 |
| WO | WO 01/89505 A1 | 11/2001 |
| WO | WO 0198265 | 12/2001 |
| WO | WO 0220481 | 3/2002 |
| WO | WO 03015699 | 2/2003 |
| WO | WO 2004015907 | 2/2004 |
| WO | WO 2004/022069 A1 | 3/2004 |
| WO | WO 2004/043902 A1 | 5/2004 |
| WO | WO 2004050021 | 6/2004 |
| WO | WO 2004064912 | 8/2004 |
| WO | WO 2004101072 | 11/2004 |
| WO | WO 2005073237 | 8/2005 |
| WO | WO 2005/094799 A2 | 10/2005 |

OTHER PUBLICATIONS

Auris Medical AG, Written Opinion and Search Report issued by the Intellectual Property Office of Singapore (I.P.O.S.), Singapore Patent Application No. 2010/035681, Aug. 23, 2010, 17 pgs.
Guitton et al., "Cochlear NMDA Receptors and Tinnitus", Audiological Medicine, vol. 2 (2004), pp. 3-7.
Guitton et al., "m-Chlorophenyipiperazine exacerbates perception of salicylate-induced tinnitus in rats", European Journal of Neuroscience, vol. 22 (2005), pp. 2675-2678.
Guutton et al., "New Pharmacological Strategies to Restore Hearing and Treat Tinnitus", Acta Otolaryngol, vol. 124 (2004), pp. 411-415.
Guitton et al., "Salicylate induces Tinnitus through Activation of Cochlear NMDA receptors", The Journal of Neuroscience, vol. 23, No. 9 (May 1, 2003), pp. 3944-3952.

(Continued)

*Primary Examiner* — Jennifer M Kim
(74) *Attorney, Agent, or Firm* — Fanelli Haag & Kilger PLLC

(57) ABSTRACT

The invention relates to methods for the prevention and/or treatment of tinnitus induced by cochlear excitotoxicity. In these methods, a pharmaceutical composition comprising an NMDA receptor antagonist is administered to an individual in need of such treatment by appropriate devices and/or formulations for local administration to the inner ear. The tinnitus to be prevented and/or treated may be provoked by acoustic trauma, presbycusis, ischemia, anoxia, treatment with one or more ototoxic medications, sudden deafness, or other cochlear excitotoxic-inducing occurrence. The invention also relates to method for the identification of compounds effective in the treatment and prevention of tinnitus by a novel screening method incorporating an electrophysiological test method.

14 Claims, 8 Drawing Sheets

(56) References Cited

OTHER PUBLICATIONS

Guitton et al., U.S. Appl. No. Office Action, 11/236,941, Oct. 2, 2009, 17 pgs.
Guitton et al., U.S. Appl. No. Requirement for Restriction/Election, 11/238,941, Mar. 5, 2009, 8 pgs.
Kaltenbach et al., "Plasticity of spontaneous neural activity in the dorsal cochlear nucleus after intense sound exposure", Hearing Research 2000 Netherlands, vol. 147, No. 1-2 (2000), pp. 282-292.
Kenmochi et al., "Salicylate and quinine affect the central nervous system", Hearing Research 1997 Netherlands, vol. 113, No, 102 (1997), pp. 110-118.
Lenarz et al., "Neural mechanisms of tinnitus", Eur. Arch. Otorhinolaryngol, vol. 249 (1993), pp. 441-446.
Puel et al., "[Treatment of tinnitus. New perspectives]" Presse Med., vol. 31(2002), pp. 1137-1143.
Searchfield et al., "Ensemble spontaneous activity in the guinea-pig cochlear nerve", Hearing Research, vol. 192 (2004) pp. 23-35.
Simpson et al., "Recent advances in the pharmacological treatment of tinnitus", Trends in Pharmacological Sciences 1999 United Kingdom, vol. 20, No. 1 (1999), pp. 12-18.
Tabuchi et al., "Effect of Ketamine, Dextromethorphan, and MK~601 on Cochlear Dysfunction Induced by Transient ischemia", Ann. Otol. Rhirioi. Laryngol., vol. 111 (2002), pp. 44-49.
Alpini, D., et al., "Tinnitus: Pharmacological Topodiagnosis," Int Tinnitus J., vol. 10(1), pp. 91-93, 2004.
Azevedo, V.M., et al., "Transdermal Ketamine as an Adjuvant for Postoperative Analgesia After Abdominal Gynecological Surgery Using Lidocaine Epidural Blockade," Anesth Analg., vol. 91(6), pp. 1479-1482, 2000.
Baguley, D.M., "Mechanisms of Tinnitus," Br Med Bull, vol. 63, pp. 195-212, 2002.
Balough, B.J., et al., "Kinetics of Gentamicin Uptake in the Inner Ear of Chinchilla Langier After Middle-Ear Administration in a Sustained-Release Vehicle," Otolaryngol Head Neck Surg., vol. 119(5), 427-431, 1998.
Barnea, G., et al., "Tinnitus with Normal Hearing Sensitivity: Extended High-Frequency Audiometry and Auditory-Nerve Brain-Stem-Evoked Responses," Audiology, vol. 29(1), pp. 36-45, 1990.
Battaglia, A., et al., "Involvement of Ras Activation in Toxic Hair Cell Damage of the Mammalian Cochlea," Neuroscience, vol. 122(4), pp. 1025-1035, 2003.
Bauer, C.A., et al., "Assessing Tinnitus and Prosepective Tinnitus Therapeutics Using a Psychophysical Animal Model," J. Assoc. Res. Otolaryngol., vol. 2(1), pp. 54-64, 2001.
Bauer, C.A., et al., "Behavioral Model of Chronic Tinnitus in Rats," Otolaryngol Head Neck Surg., vol. 121(4), pp. 457-462, 1999.
Bauer, C.A., et al., "Animal Models of Tinnitus," Otolaryngol Clin N Am, vol. 36, pp. 267-285, 2003.
Bespalov, et al., "Neuropsychopharmacology of NMDA Receptor Antagonists," S-PB, p. 28, 2000.
Binder, D.K., "The Role of BDNF in Epilepsy and Other Diseases of the Mature Nervous System," Adv Exp Med Biol, vol. 548, pp. 34-56, 2004.
Bodmer, D., et al., "Rescue of Auditory Hair Cells from Aminoglycoside Toxicity by Clostridium Difficile Toxin B, an Inhibitor of the Small GTPases Rho/Rac/Cdc42," Hear Res., vol. 172(1-2), pp. 81-86, 2002.
Boettcher, F.A., et al., "Salicylate Ototoxicity: Review and Synthesis," Am J Otolaryngol., vol. 12(1), pp. 33-47, 1991.
Borsello, T., et al., "A Peptide Inhibitor of C-Jun N-Terminal Kinase Protects Against Excitotoxicty and Cerebral Ischemia," Nat Med, vol. 9(9), pp. 1180-1186, 2003.
Cahani, M., et al., "Tinnitus Pitch and Acoustic Trauma," Audiology, vol. 22(4), pp. 357-363, 1983.
Casado, M., et al., "Opposite Modulation of NMDA Receptors by Lysohospholipids and Arachidonic Acid: Common Features with Mechanosensitivity," J Physiol., vol. 513(Pt 2), pp. 317-330, 1998.
Cazals, Y., "Auditory Sensori-Neural Alterations Induced by Salicylate," Prog Neurobiol., vol. 62(6), pp. 583-631, 2000.
Chandrasekhar, S.S., et al., "Dexamethasone Pharmacokinetics in the Inner Ear: Comparison of Rout of Administration and Use of Facilitating Agents," Otolaryngol Head Neck Surg., vol. 122(4), pp. 521-528, 2000.
Charkevic, D.A., "Pharmacology," Medicina, p. 28, 1980.
Chen, Z., et al., "Acute Treatment of Noise Trauma with Local Caroverine Application in the Guinea Pig," Acta Otolaryngol., vol. 123(8), pp. 905-909, 2003.
Chen, Z., et al., "Pharmacokinetics of Caroverine in the Inner Ear and Its Effects on Cochlear Function After Systemic and Local Administrations in Guinea Pigs," Audiol Neurootol., vol. 8(1), pp. 49-56, 2003.
Choi, D.W., et al., "Pharmacology of Glutamate Neurotoxicity in Cortical Cell Culture: Attenuation by NMDA Antagonists," J Neurosci., vol. 8(1), pp. 185-196,1988.
Chung, D.Y., et al., "Factors Affecting the Prevalence of Tinnitus," Audiology, vol. 23(5), pp. 441-452, 1984.
Ciocon, et al., "Does Oxazepam Offer Relief of Tinnitus or Alter It to a Non-Troublesome Functional Level in the Elderly?," J of the American Geriatrics Society, vol. 45(9), p. 122, 1997.
Coad, M.L., et al., "Characteristics of Patients with Gaze-Evoked Tinnitus," Otol Neurotol., vol. 22(5), pp. 650-654, 2001.
d'Aldin, C.G., et al., "Implication of NMDA Type Glutamate Receptors in Neural Regeneration and Neoformation of Synapses After Excitotoxic Injury in the Guinea Pig Cochlea," Int J Dev Neurosci., vol. 15(4-5), pp. 619-629, 1997.
Del Bo, L., et al., "Tinnitus Aurium in Persons with Normal Hearing: 55 Years Later," Otolaryngol Head Neck Surg., vol. 139(3), pp. 391-394, 2008.
Denk, D.M., et al., "Caroverine in Tinnitus Treatment. A Placebo-Controlled Blind Study," Acta Otolaryngol., vol. 117(6), pp. 825-830, 1997.
Diamond, C., et al., "Systematic Review of Intratympanic Gentamicin in Meniere's Disease," J Otolaryngol., vol. 32(6), pp. 351-361, 2003.
Dobie, R.A., "A Review of Randomized Clinical Trials in Tinnitrus," Laryngoscope, vol. 109(8), pp. 1202-1211, 1999.
Dobie, R.A., "Clinical Trials and Drug Therapy for Tinnitus," Tinnitus: Theory and Management, pp. 266-277, 2004.
Dodson, K.M., et al., "Intratympanic Perfusion for the Treatment of Tinnitus," Otolaryngol Clin North Am, vol. 37(5), pp. 991-1000, 2004.
Dolly, J.O., et al.: "The Structure and Mode of Action of Different Botulinum Toxins," Eur J Neurol, vol. 13(Suppl 4), pp. 1-9, 2006.
Domeisen, H., et al., "Caroverine in Tinnitus Treatment," Acta Otolaryngol., vol. 118(4), pp. 606-607, 1998.
Dravid, S.M., et al., "Subunit-Specific Mechanisms and Proton Sensitivity of NMDA Receptor Channlel Block," J Physiol, vol. 581(Pt 1), pp. 107-128, 2007.
Duan, M., et al., "Complementary Roles of Neurotrophin 3 and a N-Methyl-D-Aspartate Antagonist in the Protection of Noise and Aminoglycoside-Induced Ototoxicity," Proc Natl Acad Aci USA, vol. 97(13), pp. 7597-7602, 2000.
Eggermont, J.J., et al., "The Neuroscience of Tinnitus," Trends Neurosci., vol. 27(11), pp. 676-682, 2004.
Ehrenberger, K., et al., "Receptor Pharmacological Models for Inner Ear Therapies with Emphasis on Glutamate Receptors: A Survey," Acta Otolaryngol, vol. 115(2), pp. 236-240, 1995.
Ehrenberger, K., et al., "Clinical Experience with Caroverine in Inner Ear Diseases," Adv Otorhinolaryngol, vol. 59, pp. 156-162, 2002.
Ehrenberger, K., et al., "Topical Administration of Caroverine in Somatic Tinnitus Treatment: Proof-of-Concept Study," Int Tinnitus J., vol. 11(1), pp. 34-37, 2005.
Fitzgibbons, P.J., et al., "Gap Detection in Normal and Hearing-Impaired Listeners," J Acoust Soc Am, vol. 72(3), pp. 761-765, 1982.
Frank, Von I., "Synthese von Dualen NMDA-Rezeptor-/Dopamin-Rezeptor-Liganden, Dissertation, Vorgelegt Beim FB Biochemie," Chemie und Pharmazie, Johann Wolfgang Goethe-Universität Frankfurt am Main, 2005.
Gabellini, N., "Transcriptional Regulation by cAMP and Ca2+ links the Na+/Ca2+ exchanger 3 to Memory and Sensory Pathways," Mol Neurobiol., vol. 30(1), pp. 91-116, 2004.

Goycoolea, M.V., et al., "Round Window Membrane. Structure Function and Permeability: A Review," Microsc Res Tech, vol. 36(3), pp. 201-211, 1997.

Hawkins, D.B., et al., "Interaural Time Discrimination Ability of Listeners with Sensorineural Hearing Loss," Audiology, vol. 19(6), pp. 495-507, 1980.

Hoffer, M.E., et al., "Sustained-Release Devices in Inner Ear Medical Therapy," Otolaryngol Clin North Am, vol. 37(5), pp. 1053-1060, 2004.

Hoffer, M.E., et al., "Transtympanic Management of Tinnitus," Otolaryngol Cin North Am, vol. 36(2), pp. 353-358, 2003.

Horimoto, N., et al., "Developmental Changes in Arachidonic Acid Potentiation of NMDS Currents in Cortical Neurons," Neuroreport, vol. 7(15-17), pp. 2463-2467, 1996.

House, J.W., et al., "Tinnitus: Surgical Treatment," Ciba Found Symp., vol. 85, pp. 204-216, 1981.

Ito, J., et al., "A New Method for Drug Application to the Inner Ear," Orl J Otorhinolaryngol Relat Spec, vol. 67(5), pp. 272-275, 2005.

Kemp, J.A., et al., "NMDA Receptor Pathays as Drug Targets," Nat Neurosci., 5 Suppl, pp. 1039-1042, 2002.

Knipper, M., et al., "Thyroid Hormone Deficiency Before the Onset of Hearing Causes Irreversible Damage to Peripheral and Central Auditory Systems," J Neurophysiol., vol. 83(5), pp. 3101-3112, 2000.

Koester, M., et al., "Tinnitus—Classification, Causes, Diagnosis, Treatment and Prognosis", MMW Fortsch Med, vol. 146(1-2), pp. 23-24, pp. 26-28, 2004.

Kumagai, M., et al., "Effect of Intravenous Injection of Aspirin on the Cochlea," Kokkaido Igaku Zasshi, vol. 67(2), pp. 216-233, 1992.

Lang, U.E., et al., "Association of BDNF Serum Concentrations with Central Serotonergic Activity: Evidence from Auditory Signal Processing," Neuropsychopharmacology, vol. 30(6), pp. 1148-1153, 2005.

Lehner, R., et al., "A Totally Implantable Drug Delivery System for Local Therapy of the Middle and Inner Ear," Ear Nose Throat J., vol. 76(8), pp. 567-570, 1997.

Light, J.P., et al., "Transtympanic Perfusion: Indications and Limitations," Curr Opin Otolaryngol Head Neck Surg, vol. 12(5), pp. 378-383, 2004.

Lobarinas, E., et al., "Salicylate- and Quinine-Induced Tinnitus and Effects of Memantine," Acta Otolaryngol Suppl, (556), pp. 13-19, 2006.

Lockwood, A. H., et al., "The Functional Anatomy of Gaze-Evoked Tinnitus and Sustained Lateral Gaze," Neurology, vol. 56(4), pp. 472-480, 2001.

Maier, C., et al., "Efficacy of the NMDA-Receptor Antagonist Memantine in Patients with Chronic Phantom Limb Pain—Results of a Randomized Double-Blinded, Placebo-Controlled Trial," Pain, vol. 103(3), pp. 277-283, 2003.

Menkes, D.B., et al., "Sodium Valproate for Tinnitus," J. Neurol Neurosurg Psychiatry, vol. 65(5), p. 803, 1998.

Middleton, C., "The Causes and Treatments of Phantom Limb Pain," Nurs Times, (35), pp. 30-33, 2003.

Miller, B., et al., "Potentiation of NMDA Receptor Currents by Arachidonic Acid," Nature, vol. 355(6362), pp. 722-725, 1992.

Nicolas-Puel, C., et al., "Characteristics of Tinnitus and Etiology of Associated Hearing Loss: A Study of 123 Patients," Int Tinnitus J., vol. 8(1), pp. 37-44, 2002.

Niedzielski, A.S., et al., "Expression of AMPA, Kainate, and NMDA Receptor Subunits in Cochlear and Vestibular Ganglia," J Neurosci., vol. 15(3 Pt 2), pp. 2338-2353, 1995.

Oestricher, E., et al., "Different Action of Memantine and Caroverine on Glutamatergic Transmission in the Mammalian Chochlea," Adv Otorhinolaryngol, vol. 59, pp. 18-25, 2002.

Oestreicher, E., "Memantine Suppresses the Glutamatergic Neurotransmission of Mammalian Inner Hair Cells," Orl J Otorhinolaryngol Relat Spec., vol. 60(1), pp. 18-21, 1998.

Olney, J.W., et al., "Glutamate-Induced Brain Damage in Infant Primates," J Neuropathol Exp Neurol., vol. 31(3), pp. 464-488, 1972.

Pirvola, U., et al., "Rescue of Hearing, Auditory Hair Cells, and Neurons by CEP-1347/KT7515, An Inhibitor of C-Jun N-Terminal Kinase Activation," J Neurosci., vol. 20(1) pp. 43-50, 2000.

Puel, J.L., et al., "Electrophysiological Evidence for the Presence of NMDA Receptors in the Guinea Pig Cochlea," Hear Res, vol. 51(2), pp. 255-264, 1991.

Puel, J.L., et al., "Excitatory Amino Acid Antagonists Protect Cochlear Auditory Neurons from Excitotoxicty," J Comp Neurol., vol. 341 (2), pp. 241-256, 1994.

Puel, J.L., et al., "Synaptic Regeneration and Functional Recovery After Excitotoxic Injury in the Guinea Pig Cochlea," C R Acad Sci III, vol. 318(1), pp. 67-75, 1995.

Puel, J.L., et al., "Synaptic Repair Mechanisms Responsible for Functional Recovery in Various Cochlear Pathologies," Acta Otolaryngol, vol. 117(2), pp. 214-218, 1997.

Puel, J.L., et al., "The Inner Hair Cell Synaptic Complex: sphysiology, Pharmacology and New Therapeutic Strategies," Audiol Neurootol, vol. 7(1), pp. 49-54, 2002.

Puel, J.L., et al., "Chemical Synaptic Transmission in the Cochlea," Prog Neurobiol., vol. 47(6), pp. 449-476, 1995.

Pujol, R., et al., "Excitotoxicity, Synaptic Repair, and Functional Recovery in the Mammalian Cochlea: A Review of Recent Findings," Ann NY Acad Sci, vol. 884, pp. 249-254, 1999.

(i) Pujol, R., et al., Implication of Non-NMDA and NMDA Receptors in Cochlear lschemia, Neuroreport, vol. 3(4), pp. 299-302, 1992.

Reyes, S.A., et al., "Brain Imaging of the Effects of Lidocaine on Tinnitus," Hear Res, vol. 171(1-2), pp. 43-50, 2002.

Ruel, J., et al., "AMPA-Preferring Glutamate Receptors in Cochlear Physiology of Adult Guinea-Pig," J Physiol., vol. 518(Pt 3), pp. 667-680, 1999.

Ruel, J., et al., "Salicylate Enables Cochlear Arachidonic-Acid-Sensitive NMDA Receptor Responses," J Neurosci., vol. 28(29), pp. 7313-7323, 2008.

Sahley, et al., "A Biochemical Model of Preipheral Tinnitus," Hearing Research, vol. 152, pp. 43-54, 2001.

Sakata, E., et al., "Treatment of Cochlear-Tinnitus with Dexamethasone Infusion into the Tympanic Cavity," Int Tinnitus J., vol. 2, pp. 129-135, 1996.

Sala, T., "Transtympanic Administration of Aminoglycosides in Patients with Meniére's Disease," Arch Otorhinolaryngol, vol. 245(5), pp. 293-296, 1988.

Sattler, R., et al., "Molecular Mechanisms of Glutamate Receptor-Mediated Excitotoxic Neuronal Cell Death," Mol Neurobiol., vol. 24(1-3), pp. 107-129, 2001.

Scarpidis, U., et al., "Arrest of Apoptosis in Audiotry Neurons: Implications for Sensorineural Preservation in Cochlear Implantation," Otol Neurotol., vol. 24(3), pp. 409-417, 2003.

Schimmang, T., et al., "Lack of Bdnf and TrkB Signaling in the Postnatal Cochlea Leads to a Spatial Reshaping of Innervation Along the Tonotopic Axis and Hearing Loss," Development, vol. 130(19), pp. 4741-4750, 2003.

Schwab, B., et al., "Use of the Round Window Micro Cath for Inner Ear Therapy—Results of a Placebo-Controlled, Prospective Study on chronic Tinnitus," Laryngorhinootologie, vol. 83(3), pp. 164-172, 2004.

Selivanova, et al., "The Effects of Streptolysin-O and Sodium Hyaluronate on the Permeability of the Round Window Membrane in Guinea Pigs—An Electrophysiologic Study," Laryngorhinootologie, vol. 82(4), pp. 235-239, 2003.

Shulman, A., "Neurroprotective Drug Therapy: A Medical and Pharmalogical Treatment for Tinnitus Control," Int Tinnitus J, vol. 3(2), pp. 77-93, 1997.

Silverstein, H., et al., "Direct Round Window Membrane Application of Gentamicin in the Treament of Meniere's Disears," Otolaryngol Head Neck Surg., vol. 120(5), pp. 649-655, 1999.

Stypulkowski, P.H., "Mechanisms of Salicylate Ototoxicity," Hear Res., vol. 46(1-2), pp. 113-145, 1990.

Szczepaniak, W.S., et al., "Effects of L-Baclofen and D-Baclofen on the Auditory System: A Study of Click-Evoked Potentials from the Inferiro Colliculus in the Rat," Ann Otol Rhinol Laryngol, vol. 104(5), p. 399-404, 1995.

Theopold, H.M., "Nimodipine (Bay e 9736) A New Therapy Concept in Diseases of the Inner Ear," Laryngol Rhinol Otol (Stuttg), vol. 64(12), pp. 609-613, 1985.

Timmusk, T., et al., "Identification of Brain-Derived Neurotrophic Factor Promoter Regions Mediating Tissue-Specific, Axotomy-, and Neuronal Activity-Induced Expression in Transgenic Mice," J Cell Biol., vol. 128(1-2), pp. 185-199, 1995.

Togal, T., et al., "Effects of S(+) Ketamine Added to Bupivacaine for Spinal Anaethesia for Prostate Surgery in Elderly Patients," Eur J Anesthesiol, vol. 21(3), pp. 193-197, 2004.

Vane, J.R., et al., "Mechanisms of Action of Nonsteroidal Anti-Inflammatory Drugs," Am J Med, vol. 104(3A), pp. 2S-8S, Discussion 21S-22S, 1998.

Vesterarger, V., "Tinnitus-Investigation and Management," British Medical Journal, vol. 314(7082), pp. 728-731, 1997.

Vichitrananda, C., et al., "Midazolam for the Treatment of Phantom Limb Pain Exacerbation: Preliminary Reports," J Med Assoc Thai, vol. 84(2), pp. 299-302, 2001.

Vollenweider, F.X., et al., "Differential Psychopathology and Patterns of Cerebral Glucose Utilisaiton Produced by (S)- and (R)-Ketamine in Healthy Volunteers Using Positron Emission Tomography (PET)," Eur Neuropsycholpharmacol., vol. 7(1), pp. 25-38, 1997.

Waddell, A., et al., "Tinnitus," Am Fam Physcian, vol. 69(3), pp. 591-592, 2004.

Wang, H., et al., "Evaluating Effects of Some Medicine on Tinnitus with Animal Behavioral Model in Rats," Zhonghua Er Bi Yan Hou Ke Za Zhi, vol. 35(5), pp. 331-334, 2000.

Wang, J., et al., A Peptide Inhibitor of C-Jun N-Terminal Kinase Protects Against Both Aminolglycoside and Acoustic Trauma-Induced Auditory Hair Cell Death and Hearing Loss,: J Neurosci, vol. 23(24), pp. 8596-8607, 2003.

Wang, J., et al., "Effects of Selective Inner Hair Cell Loss on Auditory Nerve Fiber Threshold, Tuning and Spontaneous and Driven Discharge Rate," Hear Res, vol. 107(1-2), pp. 67-82, 1997.

Weber, W.E., "Pharmacotherapy for Neuropathic Pain Caused by Injury to the Afferent Nerve Fibers," Ned Tijdschr Geneeskd, vol. 145(17), pp. 813-817, 2001.

West, A.E., et al., "Calcium Regulation of Neuronal Gene Expression," Proc Natl Acad Sci USA, vol. 98(20), pp. 11024-11031, 2001.

Wiechers, B., et al., "A Changing Pattern of Brain-Derived Neurotrophic Factor Expression Correltates with the Rearrangement of Fibers During Cochlear Development of Rats and Mice," J Neurosci, vol. 19(8), pp. 3033-3042, 1999.

Willingham, E., "Tinnitus," Grand Rounds Archive, Baylor College of Medicine in Houston, Texas, pp. 1-8, 2004.

Yamakura, T., et al., "Subunit- and Site-Specific Pharmacology of the NMDA Receptor Channel", Prog Neurobiol., vol. 59(3), pp. 279-298, 1999.

Ylikoski, J. et al., "Blockade of C-Jun N-Termina Kinase Pathway Attenuates Gentamicin-Induced Cochlear and Vestibular Hair Cell Death," Hear Res, vol. 166(1-2), pp. 33-43, 2002.

Zine, A., et al., "The MAPK/JNK Signalling Pathway Offers Potential Therapeutic Targets for the Prevention of Acquired Deafness," Curr Drug Targets CNS Neurol Disord., vol. 3(4), pp. 325-332, 2004.

English abstract of document B4, Japanese Pat. No. JP 2001-187737.

International Pharmaceutical Excipients Council Japan translate edition, "Poloxamer", Handbook of Pharmaceutical Excipients revised edition, Yakuji Nippo Limited, pp. 910-914, Feb. 28, 2007.

Parsons et al., Memantine is a clinically well tolerated N-methyl-D-asparate (NMDA) receptor antagonist—a review of preclinical data, Neuropharmacology, 38/6):735-767, 1994.

Pfenninger E., et al., Neuroprotektion durch Ketamin auf zellularer Ebene (Neoroprotective effects of ketamine on a cellular level), Der Anaestesist, vol. 46, Suppl. 1, pp. S47-S54, 1997.

Barrs et al., "Intratympanic Steroid Injections for Intractable Meniere's Disease", The Laryngoscope, 111(12):2100-2104, 2001.

* cited by examiner

METHODS FOR THE TREATMENT OF TINNITUS INDUCED BY COCHLEAR EXCITOTOXICITY

This application is a Continuation of U.S. application Ser. No. 11/236,941, filed Sep. 28, 2005, which is a Continuation-In-Part of U.S. application Ser. No. 10/812,298, filed Mar. 29, 2004, the entire contents of all of which are incorporated herein by reference in their entirety.

BACKGROUND OF THE INVENTION

1. Field of the Invention

This invention relates to methods for the delivery of pharmaceutical compounds to the inner ear for the treatment of tinnitus induced by cochlear excitotoxicity. Specifically, this invention relates to the local administration of N-Methyl-D-Aspartate (NMDA) receptor antagonists to the inner ear to suppress the NMDA receptor mediated aberrant activity of the auditory nerve following acute, repeated or prolonged or chronic occurrences of cochlear excitotoxicity provoked by incidents such as acoustic trauma, presbycusis, ischemia, anoxia, treatment with one or more certain ototoxic medications or sudden deafness and thus, block tinnitus in the case of such incidents.

2. Description of Related Art

Tinnitus, the perception of sound without external acoustic stimulation, is a very common inner ear disorder. It is estimated that 8.6 million Americans, about 3 percent of the U.S. population, suffer from chronic tinnitus (Centers for Disease Control and Prevention, Vital and Health Statistics, Series 10, #200, October 1999). According to the American SpeechLanguage-Hearing Association (ASHA), a million or more persons find that their tinnitus prevents them from leading a normal life (0.3% of the population). European population studies estimate 7% to 14% of the population have talked with their physician about tinnitus, while potentially disabling tinnitus occurs in approximately 1% to 2.4% of people (Vesterarger V., *British Medical Journal* 314 (7082): 728-731 (1997)).

In spite of the high prevalence of tinnitus and its severe impact on the health and quality of life of people affected by it, there is no truly effective treatment available. Current therapy approaches include the avoidance of ototoxic medications, reduced consumption of alcohol, caffeine and nicotine, reduced stress, the use of background noises or wearable tinnitus maskers (some in combination with hearing aids), behavioral therapies such as hypnosis, cognitive therapy and biofeedback, tinnitus retraining therapy (TRT), pharmacological and other complementary therapies.

Tinnitus is not a disease, but rather a symptom common to various hearing disorders, just as pain accompanies many different illnesses. It is most frequently associated with noise-induced hearing loss, presbycusis and Ménière's Disease (Nicolas-Puel et al., *International Tinnitus Journal* 8 (1): 37-44 (2002)). Other, less frequent origins include exposure to ototoxic drugs (aminoglycoside antibiotics, high-dose loop diuretics, nonsteroidal anti-inflammatory drugs and certain chemotherapeutic agents), reduced vascular flow (ischemia), autoimmune processes, infectious diseases, conductive hearing loss, otosclerosis, head trauma etc. In over 90% of cases, tinnitus is associated with hearing foss of known origin, and well over 70% originate within the inner ear (Nicolas-Puel et al., *International Tinnitus Journal* 8 (1): 37-44 (2002)).

Over the past decade, major advances in the research of the physiopathology of the inner ear resulted in the identification of the key role of the inner hair cell synaptic complex in the development of tinnitus induced by cochlear excitotoxicity, one of the most frequent triggers of tinnitus. Excitotoxicity, which was first described by Olney et al., *J. Neuropathol. Exp. Neurol.* 31(3): 464-488 (1972), is generally characterized as an excessive synaptic release of glutamate, which is the most important neurotransmitter in the Central Nervous System as well as in the auditory system. It activates postsynaptic glutamate receptors (ionotropic and metabotropic), which leads to depolarization and neuronal excitation. However, if receptor activation becomes excessive by an excessive release of glutamate as in the case of excitotoxicity, the target neurons are damaged and may eventually die (Puel J. L, *Prog Neurobiol.* 47(6): 449-76 (1995)).

Cochlear excitotoxicity is provoked either by exposure to excessive noise such as in the case of acute or repeated acoustic trauma (which leads to noise-induced hearing loss or presbycusis), sudden deafness or anoxia/ischemia (Pujol and Puel, *Ann. NY Acad. Sci.* 884: 249-254 (1999)) or treatment with one or more certain ototoxic medications. The release of excessive amounts of glutamate is induced either by the excessive sound pressure entering the cochlea in case of acoustic trauma or the reduced blood flow to the glutamate regulating system in case of anoxia/ischemia respectively sudden deafness. In all cases, excitotoxicity is characterized by a two-step mechanism: first, there is an acute swelling of the type I afferent dendrites mediated by the ionotropic glutamate receptors, which leads to a disruption of the postsynaptic structures and a loss of function. Within the next 5 days, synaptic repair (neo-synaptogenesis) is observed with a full or partial recovery of cochlear potentials (Puel et al., *Acta Otolaryngol.* 117 (2): 214-218 (1997)). In the second phase of excitotoxicity, which may develop after strong and/or repetitive injury, a cascade of metabolic events triggered by the entry of $Ca^{2+}$ leads to neuronal death of the spiral ganglion neurons.

Cochlear excitotoxicity may induce tinnitus during the process of rupturing of the postsynaptic structures and, provided the rupture is not terminal, the following neo-synaptogenesis at the inner hair cell synaptic complex (Puel et al., *Audiol. Neurootol.* 7 (1): 49-54 (2002)). A key role in functional recovery after excitotoxicity is played by the NMDA receptors, which are not involved in the activity of auditory nerve fibres under physiological conditions (Puel et al., *Audiol. Neurootol.* 7 (1): 49-54 (2002)), but are up-regulated during the process of neo-synaptogenesis (Puel et al., *C. R. Acad. Sci. III.* 318 (1): 67-75 (1995)), mainly owing to their high calcium ($Ca^{2+}$) permeability (Sattler and Tymianski, *Mol. Neurobiol.* 24 (1-3): 107-129 (2001)). As could be shown in an animal model of cochlear synaptic repair mechanisms, blockage of the NMDA receptors by local administration of the NMDA receptor antagonist D-AP5 delayed the functional recovery and the regrowth of auditory dendrites (Gervais D'Aldin et al., *Int. J. Dev. Neurosci.* 15 (4-5): 619-629 (1997)). It could thus be concluded that glutamate, in addition to its role as a fast excitatory neurotransmitter, has a neurotrophic role via the activation of NMDA receptors.

It has been hypothesized that the up-regulation of mRNA of NMDA receptors induced by cochlear excitotoxicity is responsible for abnormal spontaneous "firing" of the auditory nerve fibres, which may be perceived as tinnitus (Puel J.-L. et al., *Audiol. Neurootol.* 7 (1): 49-54 (2002)). During the process of neo-synaptogenesis afferent dendrites are in a critical state, and may thus be particularly susceptible to excitation by the activation of the NMDA receptors. To avoid any such aberrant excitation, and therefore tinnitus, which may well continue infinitely due to incomplete neo-synaptogenesis, a therapeutic strategy would thus seek to specifically antagonize NMDA receptors. As has been demonstrated, the local administration of NMDA receptor antagonists to the cochlea prevents excitotoxicity induced by acoustic trauma or ischemia (Duan et al., *Proc. Natl. Acad. Sci. USA* 97 (13): 7597-7602 (2000); Puel, *Prog. Neurobiol.* 47 (6): 449-476 (1995); Puel et al., *J. Comp. Neurol.* 341 (2): 241-256 (1994)). While excitotoxicity could also be blocked by application of 2-amino-3-(3-hydroxy-5-methylisoxazol-4-yl) propionate (AMPA) or kainate receptor antagonists, as the acute swelling of afferent dendrites primarily occurs via them (Puel et al., *J. Comp. Neurol.* 341 (2): 241-256 (1994)), such an approach would have a potentially significantly negative impact on the auditory function. As fast excitatory neurotransmission between the inner hair cells and the auditory nerve fibres is predominantly mediated by AMPA preferring receptors (Ruel et al., *J. Physiol. London* 518: 667-680 (1999)), their blocking would suppress not only the undesired excessive stimulation of the auditory nerve, but also the desired, regular excitation and thus provoke hearing loss.

The hypothesized implication of NMDA receptors in the generation of tinnitus has so far only been tested and demonstrated in vivo with a behavioral model of salicylate-induced tinnitus (Guitton et al., *J. of Neuroscience* 23 (9): 3944-3952 (2003)). The behavioral model, which had to be developed to measure tinnitus, as tinnitus is not directly observable, was based on the active avoidance paradigm: the animals were conditioned to jump onto a pole whenever hearing a particular sound. Administration of salicylate led to a significant increase in the number of jumps even in the absence of external sound (false positives), indicating the perception of tinnitus. Following delivery of the NMDA antagonists MK-801, 7-CK and gacyclidine to the animals' cochleas via the round window membrane the number of false positives decreased significantly, indicating the suppression of tinnitus.

While these results provided for the first time a confirmation of the hypothesized implication of NMDA receptors in the occurrence of tinnitus, they could clearly not be generalized for all kinds of this inner ear disorder, as salicylate-induced tinnitus is a very peculiar form of tinnitus. Salicylate, the active component of aspirin, has been known for more than a century to induce tinnitus if taken in large doses (Cazals Y., *Prog. Neurobiol.* 62: 583-631 (2000)). It may provoke similar sensations of tinnitus as in the case of cochlear excitotoxicity or other cases with different origin, but it is usually reversible and based on a specific molecular mechanism. Application of mefenamate, a well known cyclooxygenase inhibitor, instead of salicylate also increased the number of false positive responses, suggesting that salicylate-induced tinnitus is related to an inhibition of cyclooxygenase pathway. While tinnitus induced by cochlear excitotoxicity is the result of a cascade of glutamate mediated processes leading to the up-regulation of mRNA of NMDA receptors, salicylate-induced tinnitus is mediated by changes in the arachidonic acid metabolism (see e.g. Cazals Y., *Prog. Neurobiol.* 62: 583-631 (2000)). Salicylate has been shown to inhibit cyclooxygenase activity (see e.g. Vane and Botting, *Am. J. Med.* 104: 2S-8S (1998)). Evidence demonstrates that arachidonic acid potentiates NMDA receptor currents (Miller et al., *Nature* 355: 722-725 (1992); Horimoto et al., *NeuroReport* 7: 2463-2467 (1996); Casado and Ascher, *J. Physiol.* 513: 317-330 (1998)). Electrophysiological studies have demonstrated that arachidonic acid increases the channel opening probability of NMDA receptor in various systems, including cerebellar granule cells, dissociated pyramidal cells, cortical neurons, and adult hippocampal slices (see e.g. Miller et al., *Nature* 355: 722-725 (1992); Horimoto et al., *NeuroReport* 7: 2463-2467 (1996); Yamakura and Shimoji, *Prog. Neurobiol.* 59: 279-298 (1999)). Unlike tinnitus induced by excitotoxicity, there is thus no morphological damage to the inner hair cell synaptic complex, and in particular to the synaptic ending, involved in salicylate-induced tinnitus.

U.S. Pat. No. 5,716,961 to Sands (incorporated herein by reference) discloses the administration of an NMDA receptor-specific antagonist for the purpose of treating tinnitus. Its neuroprotective properties in the case of glutamate excitotoxicity are demonstrated in cell culture. However, the compound's pharmacological action and efficacy under pathophysiological conditions in vivo are not shown, i.e. there is no relation to tinnitus induced by cochlear excitotoxicity. This must be considered a serious deficiency given the complexities of the inner hair cell synaptic complex. In addition, Sands teaches oral administration of the NMDA receptor antagonist, while discussing topical administration only for cases where a patient is unable to swallow or the oral route of administration is otherwise impaired. Topical administration is discussed nonspecifically in the form of "solutions, lotions, ointments, salves and the like."

Systemic administration of NMDA receptor antagonists to treat inner ear disorders is usually ineffective, as the cochlea is protected like the brain by a biological barrier. Relatively high doses to achieve a desired therapeutic effect would thus be required, but various potent side effects of NMDA receptor antagonists such as reduced learning, memory or motility significantly restrict the maximum tolerable doses. As various studies with humans for the treatment of CNS disorders by NMDA receptor antagonists have shown, plasma levels after systemic administration were consistently below those needed for maximal neuroprotection in animal models, as clinical doses had to be limited due to a number of potentially adverse CNS effects, catatonia, increased blood pressure and anaesthesia (Kemp and McKernan, *Nature Neuroscience* 5, supplement: 1039-1042 (2002)). On the other hand, it has been shown that local administration of the NMDA-AMPA receptor antagonist caroverine to the inner ear results in higher intracochlear concentrations, while avoiding high secondary concentrations in plasma and cerebrospinal fluid as seen with systemic administration (Chen et al., *Audiol. Neurootol.* 8: 49-56 (2003)).

U.S. Pat. No. 6,066,652 to Zenner et al. (incorporated herein by reference) discloses a method for treating tinnitus through administration of adamantane, a known NMDA receptor antagonist. The inventors cite results from a clinical study with systemic administration which showed a reduction in tinnitus during treatment. Hypotheses brought forward to explain the results obtained centre on outer hair cells and the presynapse, and do not specifically cover the role of NMDA receptors.

While there are several indications supporting the hypothesis that NMDA receptors play an important role in the genesis of tinnitus induced by cochlear excitotoxicity, the foregoing discussion shows that the molecular mechanisms are still unclear, and that it is therefore not possible to predict reliably whether the use of NMDA receptor antagonists will effectively block this particular type of tinnitus. Further pathophysiological studies on the generation of tinnitus are thus required to validate the hypothesis and develop specific and truly effective therapeutic strategies.

SUMMARY OF THE INVENTION

The invention relates to methods for preventing and/or treating tinnitus induced by cochlear excitotoxicity in a human. The methods include administering to a human a therapeutically effective amount of a pharmaceutical composition comprising an NMDA receptor antagonist. In a method for treating tinnitus, the NMDA receptor antagonist administered is effective to suppress or reduce NMDA receptor mediated aberrant activity of the auditory nerve in the human in need of such treatment. In a method for preventing tinnitus, the NMDA receptor antagonist administered is effective to prevent NMDA receptor mediated aberrant activity of the auditory nerve in the human in need of such treatment. The tinnitus to be prevented and/or treated may be provoked by acoustic trauma, presbycusis, ischemia, anoxia, treatment with one or more ototoxic medications, sudden deafness, or other cochlear excitotoxic-inducing occurrence.

The present invention also relates to novel methods for the screening of compounds for the treatment and prevention of tinnitus wherein the method utilizes an electrophysiological method of measuring and quantifying the extent of tinnitus. The methods include the administration to a test animal of a test compound wherein the test animal, for example, comprises an electrode in contact with the round window membrane of the ear. The electrode is used to measure the ensemble spontaneous activity (ESA) of the ear where a spectral peak at about 200 to 250 Hz is indicative of tinnitus. The administration of test compounds to the animal, to the round window membrane or to the inner ear is embodied in the present invention. The animal may have acquired tinnitus by, for example, acustic trama, presbycusis, ischemia, anoxia, treatment with one or more ototoxic medications, sudden deafness, or other equivalent cochlear excitotoxic-inducing occurrence.

DETAILED DESCRIPTION OF THE INVENTION

Overview

Figure 1:
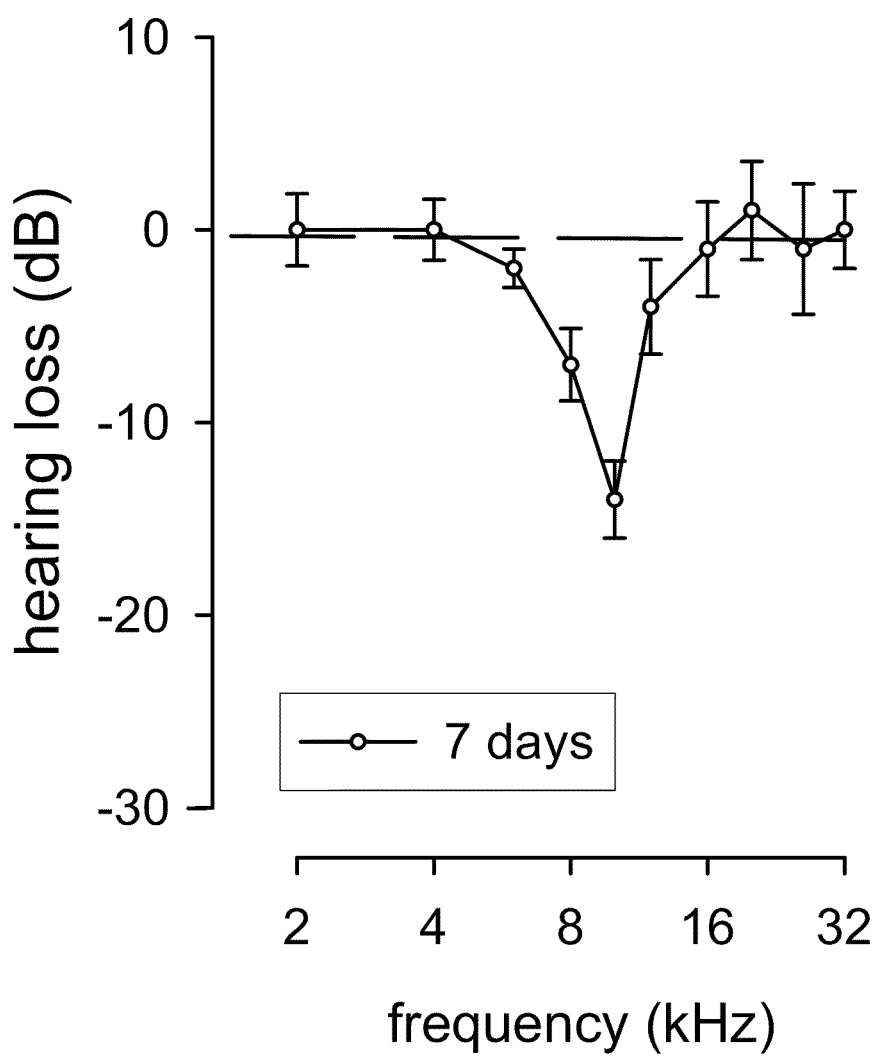
FIG. 1 shows CAP measurements 7 days after trauma in control animals. Hearing loss induced by acoustic trauma was assessed by recording CAP measurements 7 days after trauma. A permanent threshold shift of maximally 13 dB±2.0 was observed at 10 kHz on the seventh day following acoustic trauma.

The present invention is based on experimental findings with an animal model of tinnitus induced by cochlear excitotoxicity. The invention relates to the use of pharmaceutical compounds that act specifically as NMDA receptor antagonists. While not wishing to be bound by theory, it is believed that an NMDA receptor antagonist of the present invention binds to the NMDA receptor at one of its various binding sites, thereby blocking (partly or entirely) the opening of the receptor's ion channel. The NMDA receptor is activated in a complex manner such that both glutamate and glycine binding are required to open the ion channel and permit calcium entry (Kemp and McKernan, *Nature Neuroscience* 5, *supplement:* 1039-1042 (2002)). Glutamate has the neurotransmitter role, as it is released from presynaptic terminals in an activity-dependent manner, whereas glycine acts as a modulator, which is present in the extracellular fluid at more constant levels. The ion-channel integral to the NMDA receptor is voltagedependently blocked by magnesium, and depolarization removes this block. Binding of an NMDA receptor antagonist to either of the three antagonist sites results in partial or complete blockage of the NMDA receptor and hence blocks or reduces the opening of the ion channel and depolarization of the neuron. The NMDA receptor antagonist thus suppresses the aberrant excitation of the auditory nerve through up-regulated NMDA receptors which may follow cochlear excitotoxicity and thus also reduces or eliminates the perception of tinnitus. Following delivery of the NMDA receptor antagonist, the NMDA receptors are no longer up-regulated. By targeting specifically NMDA receptors, which are only up-regulated under pathophysiological conditions, to suppress the NMDA receptor mediated aberrant activity of the auditory nerve, undesired side-effects on hearing can be avoided, as normal auditory neurotransmission is primarily mediated by AMPA receptors.

In one embodiment, the invention relates to a method for treating tinnitus induced by cochlear excitotoxicity in a human. The method comprises administering to a human a therapeutically effective amount of a pharmaceutical composition comprising an NMDA receptor antagonist. The NMDA receptor antagonist is administered in an amount and for a period of time, effective to suppress or reduce NMDA receptor-mediated aberrant activity of the auditory nerve in a human in need of such treatment. Suppression or reduction of the NMDA receptor-mediated aberrant activity of the auditory nerve results in suppression or reduction of the tinnitus in the treated individual. In a preferred embodiment of this method, the NMDA receptor antagonist is administered after or during the human's exposure to a cochlear excitotoxic-inducing occurrence.

In another embodiment, the invention relates to a method for preventing tinnitus induced by cochlear excitotoxicity in a human. This method comprises administering to a human a therapeutically effective amount of a pharmaceutical composition comprising an NMDA receptor antagonist. In this method the NMDA receptor antagonist is administered in an amount and for a period of time, effective to prevent NMDA receptor-mediated aberrant activity of the auditory nerve in an individual in need of such treatment. Prevention of NMDA receptor-mediated aberrant activity of the auditory nerve prevents tinnitus in the treated individual. In a preferred embodiment of this method, the NMDA receptor antagonist is administered prior to or during the human's exposure to a potential cochlear excitotoxic-inducing occurrence. It is an object of the present invention to prevent and/or treat tinnitus which has been induced by cochlear excitotoxicity. It is not a requirement that the tinnitus induced by cochlear excitotoxicity be provoked by any specific type of occurrence, only that the occurrence provoke cochlear excitotoxicity and induce tinnitus. It is not necessarily a requirement that the nature of the occurrence be known in preventing and/or treating tinnitus. The tinnitus prevented and/or treated may be acute, subacute, or chronic.

In another embodiment, the present invention relates to methods of screening compounds for the treatment and/or prevention of tinnitus. The methods of the present invention comprise the administration of a compound to an animal that has tinnitus as measured by an ensemble spontaneous activity (ESA) with a spectral peak centered at about 200 to 250 Hz. Such conditions may be caused by, for example, acoustic trauma such as, for example, cochlear excitotoxicity. The compound may be administered, for example, locally, to the cochlear round window membrane or directly into the inner ear. The reduction in the ensemble spontaneous activity (ESA) with a spectral peak centered at about 200 to 250 Hz to a lower value is indicative of a reduction in the level of tinnitus experienced by the animal. The level in the reduction of the ESA can be compared to either, for example, a control animal suffering from tinnitus treated with a control agent, the untreated (or control agent treated) ear on the test animal or historic data. Although the methods of the present invention can be used to screen any compound for the ability to treat tinnitus, in a preferred embodiment, the compound is an NMDA receptor antagonist. The ESA measurement is obtained, for example, through an electrode in contact with the round window membrane of the ear and is read in relationship to a second electrode located in another part of the body such as, for example, neck muscle. It is another aspect of the present invention that tinnitus may be induced, for example, by exposing the animal to acoustic trauma, an example of which is subjecting the animal to a noise of about 130 dB at about 6 kHz for about 40 minutes.

In another embodiment, the present invention also relates to an electrophysical method for identifying compounds effective in the prevention of Tinnitus. In one embodiment, the method comprises administering a test compound to a test animal and exposing both the test animal and a control animal to conditions capable of inducing tinnitus as determined by measuring the ESA to determine if the spectral peak at about 200 to 250 Hz, wherein the reduction of the spectral peak at about 200 to 250 Hz in the test animal as compared to the control animal is indicative of the prevention of tinnitus. Although the methods of the present invention can be used to screen any compound for the ability to prevent tinnitus, in a preferred embodiment, the compound is an NMDA receptor antagonist. The ESA measurement is obtained, for example, through an electrode in contact with the round window membrane of the ear and is read in relationship to a second electrode located in another part of the body such as, for example, neck muscle.

It is known in the art that tinnitus results from cochlear excitotoxicity following acoustic trauma, prebycusis, ischemia, anoxia, treatment with one or more certain ototoxic medications and/or sudden deafness. The prevention of tinnitus induced by acoustic trauma is exemplified herein. One of skill in the art would predict with a high degree of certainty that the methods provided herein would be effective in preventing and/or treating tinnitus induced not only by acoustic trauma, but also by prebycusis, ischemia, anoxia, treatment with one or more certain ototoxic medications and/or sudden deafness since tinnitus resulting from all such occurrences share a common mechanistic cause. The acoustic trauma, prebycusis, ischemia, anoxia, treatment with one or more certain ototoxic medications and/or sudden deafness may be characterized as acute, repeated, or prolonged. One of skill in the art would predict that the methods of the present invention would be effective in preventing and/or treating tinnitus induced by means other than acoustic trauma, prebycusis, ischemia, anoxia, treatment with one or more certain ototoxic medications and/or sudden deafness as long as the tinnitus is induced by cochlear excitotoxicity. The cochlear excitotoxicity resulting from such occurrences may be characterized as acute, repeated, or prolonged, depending on the duration of the cochlear excitotoxic-inducing occurrence.

The term "ototoxic medication," as used in the context of the present invention, is intended to mean any compound characterized by the ability to induce tinnitus via cochlear excitotoxicity upon therapeutic administration. Cochlear excitotoxicity arises as a side-effect of the administration of ototoxic medications, which are generally administered as therapeutic compounds for treating conditions which may be unrelated to hearing or hearing perception. Ototoxic medications characterized as such include, for example, aminoglycoside antibiotics and chemotherapeutic agents such as cisplatin. Correlation of use of such ototoxic medications with cochlear excitotoxicity and the incidence of tinnitus is well known in the art, but prior to the present invention, no effective treatment has been available. The use of many such medications is currently limited by their ototoxic effects, and as such a method for reducing these effects would enable such medications to be used more widely as therapeutics. "Ototoxic," as used in the context of the present invention, is intended to mean any compound characterized by having a deleterious effect upon either the eighth nerve or upon the organs of hearing and balance.

Compound

Formulations of the pharmaceutical compounds to be administered in connection with the methods of the present invention comprise a selective NMDA receptor antagonist which binds to the NMDA receptor either at the competitive NMDA antagonist binding site, the non-competitive NMDA antagonist binding site within the ion channel, or to the glycine site. Exemplary compounds include, but are not necessarily limited to, ifenprodil, Ketamine, memantine, dizocilpine (MK-801), gacyclidine, traxoprodil (non-competitive NMDA antagonists), D-2-amino-5-phosphonopentanoic acid (D-AP5), 3-((±)$_2$-carboxypiperazin-4-yl)-propyl-1-phosphonic acid (CPP), conantokins (competitive NMDA antagonists), 7-chlorokynurenate (7-CK), and Licostinel (glycine site antagonists). An NMDA antagonist for use in the present invention may be any derivative, analogue, and/or enantiomeric form of an NMDA antagonist thereof which retains the function of an NMDA antagonist. The composition for administration in the methods of the present invention may comprise one or more NMDA receptor antagonists.

Ketamine, one of the preferred compounds of the present invention, belongs to the class of arylcycloalkylamines, and any derivative, analogue, and/or enantiomeric form of ketamine or arylcycloalkylamine that retains the function of an NMDA antagonist may be used in conjunction with the present invention. Amongst the class of arylcycloalkylamines compounds having the general formula I,

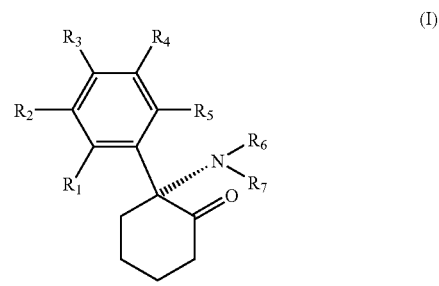

(I)

wherein R1, R2, R3, R4 and R5 independently are H, Cl, F, I, $CH_3$, $CH_2CH_3$, $NH_2$, OH or COOH and wherein R6 and R7 are independently H, $CH_3$, $CH_2CH_3$, OH, Cl, F, or I may be preferred.

A preferred arylcycloalkylamine is ketamine ($C_{13}H_{16}ClNO$ (free base), 2-(2-chlorophenyl)-2-(methylamino)-cyclohexanone), the structural formula of which is represented by formula II.

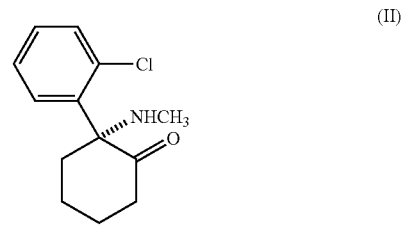 [SMILES: CN[C@@]1(c2ccccc2Cl)CCCCC1=O]

(II)

Ketamine is a non-competitive NMDA-receptor antagonist which binds to the PCP-binding site, a separate site of the NMDA-receptor complex located within the ion channel, thereby blocking the transmembranous ion flux. Ketamine may be provided by methods disclosed in U.S. Pat. No. 3,254,124. More specifically, the preferred compound is (S)-Ketamine, as it binds with a 3-4-fold higher affinity to the PCP binding site of the NMDA receptor than (R)-ketamine (Vollenweider et al., *Eur. Neuropsychopharmacol.* 7: 25-38 (1997)). The synthesis of the optical isomers may be carried out as described by DE 2062620 or WO01/98265, which are incorporated herein by reference. In a preferred embodiment of the present invention ketamine may also be administered as hydrochloride salt ($C_{13}H_{17}Cl_2NO$) of its free base form (ketamine hydrochloride).

Another preferred compound, 7-chlorokynurenate (7-CK), is represented by the following structure of formula III.

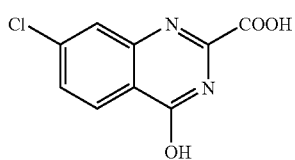

(III)

Any derivative or analogue of 7-CK may also be used in methods of the present invention.

Administration and Formulation

Delivery of the compound to patients can be accomplished orally, intravenously, subcutaneously, intraperitoneally, intramuscularly, rectally or topically, whereas topical administration to the inner ear is generally preferred, as therapeutically effective doses with systemic administration may induce undesired side-effects. One of skill in the art will recognize that administration of an NMDA antagonist in the present invention may be accomplished in a variety of other ways. The only requirement for administration in the present invention is that a therapeutically effective amount of a pharmaceutical composition comprising an NMDA antagonist be able to reach the site of the NMDA receptor mediated aberrant activity of the auditory nerve in the afflicted individual.

Administration of the compound to the inner ear may be accomplished by various delivery techniques. These include the use of devices or drug carriers to transport and/or deliver the compound in a targeted fashion to the membranes of the round or oval window, where it diffuses into the inner ear or is actively infused. Examples are otowicks (see e.g. U.S. Pat. No. 6,120,484 to Silverstein, incorporated herein by reference), round window catheters (see e.g. U.S. Pat. Nos. 5,421,818; 5,474,529; 5,476,446; 6,045,528; all to Arenberg, or U.S. Pat. No. 6,377,849 and its division 2002/0082554 to Lenarz, all of which are incorporated herein by reference), or various types of gels, foams, fibrins or other drug carriers, which are placed in the round window niche or on the oval window, and loaded with the compound for sustained release (see e.g. WO 97/38698 by Manning; Silverstein et al., *Otolaryngology—Head and Neck Surgery* 120 (5): 649-655 (1999); Balough et al., *Otolaryngology—Head and Neck Surgery* 119 (5): 427-431 (1998)). They further include the use of devices which are inserted into the cochlear duct or any other part of the cochlea (see e.g. U.S. Pat. No. 6,309,410 to Kuzma, incorporated herein by reference). The compound may also be administered to the inner ear by transtympanic injection, where the middle ear or part of it is filled by a solution or other carriers of the compound (see e.g. Hoffer et al., *Otolaryngologic Clinics of North America* 36 (2): 353-358 (2003)). The preferred method of administration to the inner ear is by diffusion across the round window membrane, which is relatively easily accessible from the middle ear space, and allows the inner ear to remain intact, thus avoiding any potential problems from leaking intracochlear fluids.

A compound contained within the pharmaceutical composition of this invention may be provided in the form of a pharmaceutically acceptable salt. Examples of such a salt include, but are not limited to, those formed with organic acids (e.g. acetic, lactic, citric, malic, formaric, tartaric, stearic, ascorbic, succinic, benzoic, methanesulfonic, toluenesulfonic, or pamoic acid), inorganic acids (e.g., hydrochloridic, nitric, diphosphoric, sulphuric, or phosphoric acid), and polymeric acids (e.g., tannic acid, carboxymethyl cellulose, polylactic, polyglycolic, or copolymers of polylactic-glycolic acids).

Pharmaceutical compositions for any route of administration of this invention contain a therapeutically effective amount of active ingredient, and, as may be necessary, inorganic or organic, solid or liquid pharmaceutically acceptable carriers. Pharmaceutical compositions suited for topical administration to the inner ear include aqueous solutions or suspensions, which, e.g. in the case of lyophilized formulations that contain the active ingredient alone or together with a carrier, may be prepared prior to use. They further include gels, which may be biodegradable or non-biodegradable, aqueous or non-aqueous, or microsphere based. Examples of such a gel include, but are not limited to, poloxamers, hyaluronates, xyloglucans, chitosans, polyesters, poly(lactides), poly(glycolide) or their co-polymers PLGA, sucrose acetate isobutyrate, and glycerol monooleate. Pharmaceutical compositions suited for enteral or parenteral administration include tablets or gelatine capsules or aqueous solutions or suspensions as described above.

The pharmaceutical compositions may be sterilized and/or may contain adjuvants, e.g. preservatives, stabilizers, wetting agents and/or emulsifiers, salts for regulating the osmotic pressure and/or buffers. The pharmaceutical compositions of the invention may, if desired, contain further pharmacologically active substances. They may be prepared by any of the methods well known in the art of pharmacy, e.g. by conventional mixing, granulating, confectioning, dissolving or lyophilizing methods, and contain from about 0.01 to 100%, preferably from about 0.1 to 50% (lyophilisates up to 100%), of active ingredient.

In a preferred embodiment the pharmaceutical composition according to the invention is formulated for topical application. Suitable vehicles for otic administration are organic or inorganic substances, which are pharmaceutically acceptable and which do not react with the active compounds, for example saline, alcohols, vegetable oils, benzyl alcohols, alkylene glycols, polyethylene glycols, glycerol triacetate, gelatin, carbohydrates such as lactose or starch, magnesium, stearate, talc and petrolatum. The indicated preparations can be sterilized and/or contain ancillary substances such as lubricants, preservatives, such as thiomersal (e.g., at 50%), stabilizers and/or wetting agents, emulsifiers, salts to influence the osmotic pressure, buffer substances, colorants, and/or aromatizing substances. They can, if required, also contain one or more other active ingredients. Otic compositions in accordance with the present invention can comprise various ingredients, including other biologically-active-agents, such as antibiotics, e.g., fluoroquinolones, anti-inflammatory agents, e.g., steroids, cortisone, analgesics, antipyrine, benzocaine, procaine, etc.

Compositions of the present invention for topical administration can comprise other ingredients which are pharmaceutically-acceptable. In preferred embodiments of the present invention, a topical excipient is selected that does not enhance delivery of the agent to the systemic circulation or to the central nervous system when administered to the ear. For example, in general, it is preferred that the topical excipient not have substantial occlusive properties, which enhance percutaneous transmission through the mucosa into the systemic circulation. Such occlusive vehicles include hydrocarbon bases, anhydrous absorption bases such as hydrophilic petrolatum and anhydrous lanolin (e.g., Aquaphor), and water-in-oil emulsion bases such as lanolin and cold cream. More preferred are vehicles which are substantially non-occlusive and, generally, include those which are water-soluble, such as oil-in-water emulsion bases (creams or hydrophilic ointments) and water-soluble bases such as polyethylene glycol-based vehicles and aqueous solutions gelled with various agents such as methylcellulose, hydroxyethyl cellulose and hydroxypropylmethylcellulose (e.g., K Y Gel).

Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87. For instance, biologicallyactive agents in accordance with the present invention can be combined with enhancing agents which enhance the penetration of an agent.

The compound can be administered prior to, during or after tinnitus has been induced by excitotoxicity. The amount to be administered may vary, depending upon the method of administration, duration of therapy, the condition of the subject to be treated, the severity of tinnitus and the efficacy of the particular compound used, age, body weight, general state of health, sex, diet, time and route of administration, rate of excretion and drug combination ultimately will be decided by the attending physician. The duration of therapy may range between about one hour and several days, weeks or months, and may extend up to chronic treatment. The therapeutically effective amount of the compound to be delivered may range between about 0.1 nanogram/hour to about 100 micrograms/hour. The substances of the invention are normally administered analogously to other otically-administered compounds. For example, ketamine can be otically administered in an amount to treat tinnitus, preferably in dosages of about 10 μg/30 ml to about 10,000 μg/30 ml, preferably about 500 μg/30 ml, or about 0.01-2 μg per dosage. By the term "dosage" for topical administration, it is meant the amount of agent administered in a single treatment, e.g., about 0.05-1 μg ketamine administered to the ear in two drops. Other anti tinnitus agents mentioned herein can be administered analogously, taking into account the potency of the drug.

A therapeutically effective dose is defined as an amount effective to suppress or reduce NMDA receptor-mediated aberrant activity of the auditory nerve in a treated individual. A therapeutically effective dose is also the amount effective to suppress or reduce tinnitus in the afflicted individual. As stated above, a therapeutically effective dose may vary, depending on the choice of specific NMDA antagonist for treatment and on the method of its administration. For example, a higher dose of an intravenously administered NMDA antagonist would be required than that of the same pharmaceutical composition administered locally to the round window membrane or oval window of the ear. Additionally, a lower dose of an NMDA antagonist would be required wherein the NMDA antagonist of the present invention binds the NMDA receptor with a higher binding affinity than an NMDA antagonist that binds with a lower affinity. As a result, NMDA antagonists with higher binding affinities for the NMDA receptor are preferred. As stated above, (S)-Ketamine, which binds with a 3-4-fold higher affinity to the PCP binding site of the NMDA receptor than (R)-ketamine (Vollenweider et al., *Eur. Neuropsychopharmacol.* 7: 25-38 (1997)) is a preferred compound for use in the methods of the present invention. The duration of therapy may also vary, depending on the specific form of tinnitus for which treatment is desired—acute, subacute, or chronic. As a guide, shorter durations of therapy are preferred and are sufficient when the tinnitus does not recur once therapy has ceased. Longer durations of therapy may be employed for an individual in which tinnitus persists following short therapy.

The findings disclosed herein relating to the treatment or prevention of tinnitus, may allow for the manufacture of a medicament for the treatment or prevention of tinnitus, particularly induced by cochlear excitotoxicity. In the manufacture of such a medicament, a compound of the class of arylcycloalkylamines, preferably of general formula I or more preferably the arylcycloalkylamine ketamine represented by formula II may be used. An NMDA receptor antagonist selected from the group consisting of 7-chlorokynurenate, D-AP5, MK 801 and gacyclidine may also be used. Moreover, it is preferred to use a pharmaceutical composition according to the invention which is formulated for topical application, in particular as a solution, gel or other controlled release formulation, an ointment or a cream or by means of an invasive drug delivery techniques, respectively, to be administered topically via the round window membrane or the oval window membrane to the inner ear or directly into the inner ear.

EXEMPLIFICATION

Example 1

Methods and Materials

We developed and tested an animal model of tinnitus induced by cochlear excitotoxicity, which was provoked by acoustic trauma. As tinnitus in general is not directly observable, as cochlear excitotoxicity does not result in tinnitus in all individuals, and as perceptions of tinnitus may just disappear a few hours after the excitotoxic incident or last forever, the definition and implementation of such an animal model represented a substantial challenge. These considerations mean for example that more animals are required to obtain a sufficient number of tinnitus cases for study and to permit observation of tinnitus over time. As it is unclear whether a case of tinnitus induced by cochlear excitotoxicity is to last or not, it is advisable to conduct studies in its early stages.

The experiments were performed in two stages. First, the hearing loss following acute acoustic trauma as well as the incidence of tinnitus were evaluated with no therapeutic compound administered. In the second stage, the efficacy of three pharmaceutical compounds in suppressing tinnitus was tested: S-(+)-Ketamine, a NMDA receptor antagonist (Sigma-Aldrich), 7-chlorokynurenate (7-CK; Sigma-Aldrich), another NMDA receptor antagonist, which was previously tested in a model of salicylate induced tinnitus (Guitton et al., *J. of Neuroscience* 23 (9): 3944-3952 (2003)) as a reference, and D-JNKI-1, a peptide inhibitor of c-Jun N-Terminal kinase (Xigen S.A.), which was shown to protect against auditory hair cell death and hearing loss due to acoustic trauma (Wang et al., *J. of Neuroscience* 23 (24): 8596-8607 (2003)). Experimental results from the first stage (i.e. no pharmaceutical compound used) served as a control.

Animals

Experiments were performed with Long-Evans rats for their superior locomotor capacities compared to other rats. During experiments, animals were caged individually at a constant temperature with a day/night cycle of 12/12 hours. All behavioral tests were performed in the dark phase, the usual period of animal activity, for every animal individually at about the same time each day. Outside the experiments, the animals received water and nutrition ad libidum. A total of 60 animals were used: 30 for the first stage (of which 25 were tested by behavioral techniques and 5 by electrophysiology), and 30 for the second stage with 10 for each pharmaceutical compound tested.

Acute Acoustic Trauma

Acoustic trauma was induced by a continuous pure tone of 6 kHz generated by a waveform synthesizer (Hewlett-Packard 8904A). The animals were anesthetized and exposed to 130 dB sound pressure level (SPL) for 20 minutes, which was routed through a programmable attenuator and presented to the ears in free field via a JBL 075 earphone positioned 10 cm in front of the animal's head. Sound level was measured using a calibrated Bruel and Kjaer microphone (4314) and a Bruel and Kjaer calibrating amplifier (2606).

Behavioral conditioning and testing Animals were conditioned to achieve active avoidance (Guitton et al., *J. of Neuroscience* 23 (9): 3944-3952 (2003)). Behavioral testing consisted of the performance of a task whenever a sound was produced in a conditioning box with an electrical floor and a climbing pole. Animal conditioning was achieved in a total of 10 sessions, each lasting between 15 and 20 minutes, with a conditioning stimulus of a pure tone at 50 dB SPL of 3 seconds duration at a frequency of 10 kHz. The unconditional stimulus consisted of an electric shock to the feet of the animals (3.7 mA) during maximally 30 seconds. Interstimulus intervals were 1 second. The electric shocks were stopped by the investigator once the animal correctly climbed onto the pole. Intervals between trials were at least one minute long.

The score was defined as the animal's performance, measured by the number of cases when it climbed correctly onto the pole in response to the sound. As soon as an animal had reached a score of at least 80% in three consecutive sessions, it was considered successfully conditioned and employed in the experiments.

Experiments were conducted daily with measurements of both score and false positive responses during one session of 10 minutes with 10 trials in total. False positive responses were climbings onto the pole between trials without any acoustic stimulation, i.e. during periods of silence. They can be interpreted as the perception of tinnitus, as the animals are performing the task of climbing onto the pole as if they were hearing the stimulus (Guitton et al., *J. of Neuroscience* 23 (9): 3944-3952 (2003)). Sound stimuli were randomized, and electrical footshocks were only delivered if the animals didn't climb onto the pole in response to sound.

Electrophysiology

The compound action potential (CAP) of the auditory nerve was measured by an electrode implanted onto the round window membrane of the animals (with a reference electrode placed in a neck muscle). The reference electrode and the round window electrode were soldered to a plug fixed on the skull. 10 tone bursts per second (with a duration of 9 ms and a rise/fall cycle of 1 ms) generated by an arbitrary function generator (LeCroy Corp., model 9100R), were applied to the animal's ear in free filed via a JBL 075 earphone. 10 frequencies were tested (2, 4, 6, 8, 10, 12, 16, 20, 26, and 32 kHz) with burst levels from 0 to 100 dB SPL in steps of 5 dB. Auditory nerve responses were amplified (Grass P511K, Astro-Med Inc.), filtered (100 Hz to 3 kHz) and averaged on a PC (Dimension Pentium, Dell). CAP amplitudes were measured peak-to-peak between the first negative depression N1 and the subsequent positive wave P1. The CAP threshold was defined as the sound intensity (in dB SPL) needed to elicit a measurable response (greater than 5 µV).

Pharmacology

Animals were anaesthetized with a single-dose i.p. injection of 0.3 ml/kg of pentobarbital at 6% (Sanofi) and operated under aseptic conditions right after the first behavioral testing (day 0). The two bullae were opened through a posterior auricular surgical procedure (dorsal approach). After exposure of the two cochleas, gelfoam (Gelita tampon, B. Braun Medical AG) impregnated with 2.5 µl artificial perilymph containing the pharmaceutical compounds was placed on the each of the round windows of the two cochleas. The concentration of all three pharmaceutical compounds used was 50 µM. The bullae were then closed with dental cement (Unifast Trad, GC Corporation), the wounds disinfected and sutured. The animals were then exposed to the traumatizing sound. Behavioral tests were resumed 24 hours after the acoustic trauma (day 1), and repeated daily for a total of 8 days.

Statistics

In each behavioral experiment, comparisons of the relevant parameters were made according to a two-way (group×time, with repeated measures on the last factor) analysis of variance (ANOVA) in order to test the measurement effect (group effect), the time effect and the group×time interactions. The ANOVA was followed by post hoc comparisons (Tukey test). Statistical analysis of CAP measurements were made according to a one-way ANOVA followed by Dunnett test. All results were presented as mean±SEM.

Results

Stage 1, No Therapeutic Compound Administered

As expected, the traumatizing sound led to a permanent hearing loss (5 animals tested with electrophysiology). As shown in FIG. 1, a permanent threshold shift of maximally 13 dB±2.0 could be observed at 10 kHz on the $7^{th}$ day after the acoustic trauma (which had occurred on day 1).

Figure 2:
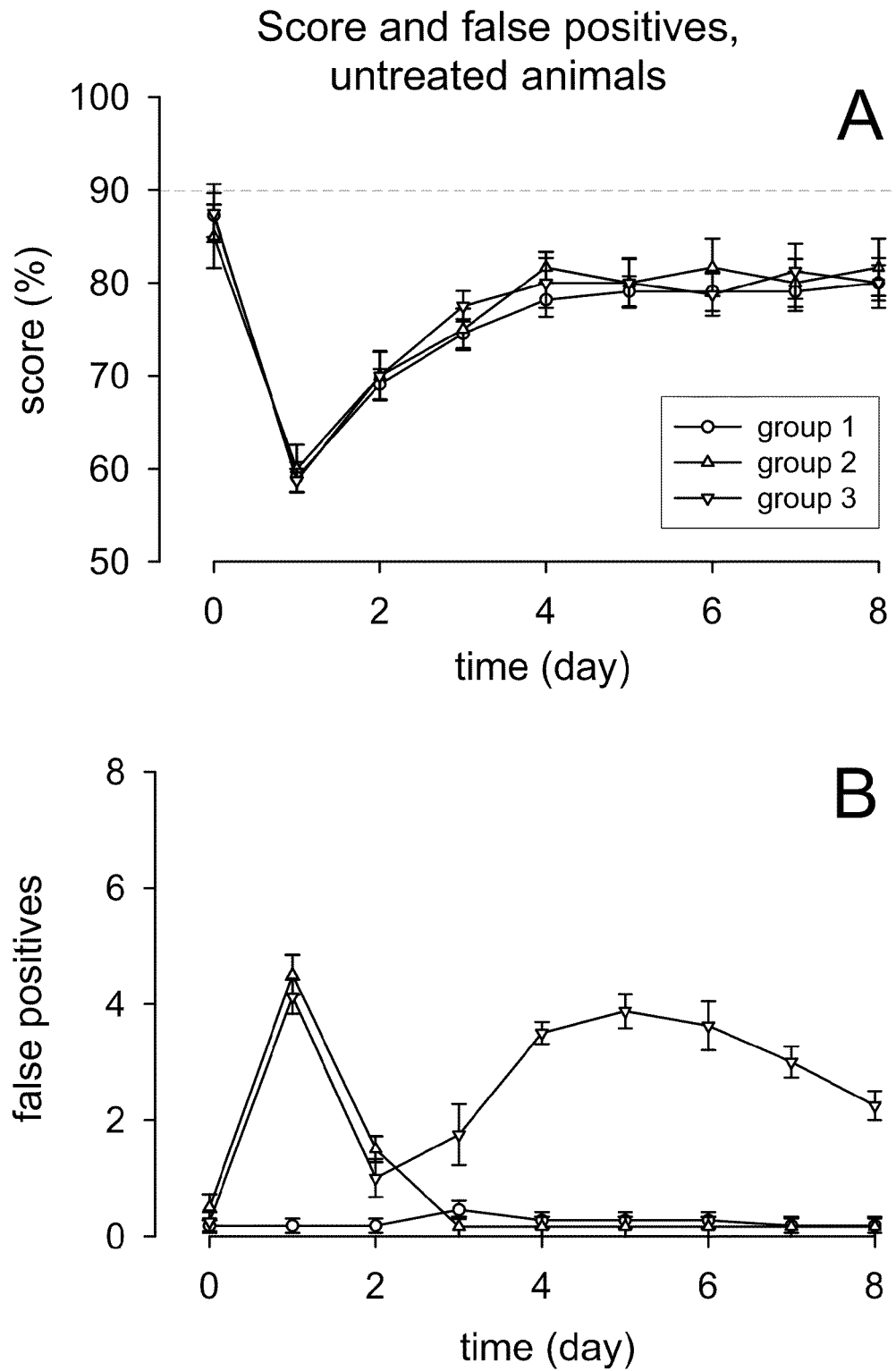
FIG. 2 illustrates the measurement of score and false positive responses following acoustic trauma in control animals. (A) Acoustic trauma led to a decrease in correct behavioral responses to sound stimulation, followed by partial recovery over time, reflecting the induced hearing loss. (B) The number of false positives differed substantially among tested animals following acoustic trauma. Group 1 animals did not experience tinnitus, group 2 animals experienced tinnitus only transiently, while group 3 animals experienced tinnitus both transiently and then permanently.

The acoustic trauma also led to a decrease in score (25 animals tested in the behavioral model). As shown in FIG. 2A, the average score dropped significantly from the high initial level of day 0 (i.e. before the acoustic trauma) of 87%±1.6 to a low of 59%±1.0 on day 1, where the acoustic trauma was provoked ($p<0.001$). Partial functional recovery could be observed from day 2 (69%±1.2), leveling off on day 4 at an average score of 80%±2.0. Statistical analysis of the results showed that the observed decreases in score were significant ($p<0.05$), also from day 2 to day 8 (80%±1.4 on the last day). The reduced ability of animals to react correctly to the conditioned sound stimulus is consistent with the fact that the hearing loss provoked by the traumatizing sound has significantly reduced their ability to hear sound at the frequency of the acoustic stimulus.

Interestingly, it was also found that the number of false positives differed substantially among the animals tested after the acoustic trauma, as shown in FIG. 2B. One group of animals (designated as group 1; n=11) displayed no increase in the number of false positives at all—even after the acoustic trauma (0.18 false positives±0.12 on days 0 and 1). The remaining 14 animals however delivered a significant increase of false positives from 0.34±0.13 on day 0 to 4.28±0.22 on day 1. This rise turned out to be reversible for 6 of them (group 2), with the number of false positives dropping to normal levels again on day 2 and thereafter. The other 8 animals however (group 3) delivered after the transitory increase yet another rise in false positives. The maximum of false positives in this second phase was observed on day 5 with 3.87±0.29, and the effect remained statistically significant through day 8 (2.25±0.25 false positives on that last day of observation). In other words: there was first a reversible increase, which was then followed by a permanent increase in the number of false positive responses to the sound stimulus. This means that after acoustic trauma some animals were experiencing no tinnitus at all (group 1), some only in a transitory form (group 2), and some first in a transitory form and then permanently again for the rest of the observation period. This outcome corresponds in principle to general observations in humans.

Stage 2, Application of Therapeutic Compounds

Figure 3:
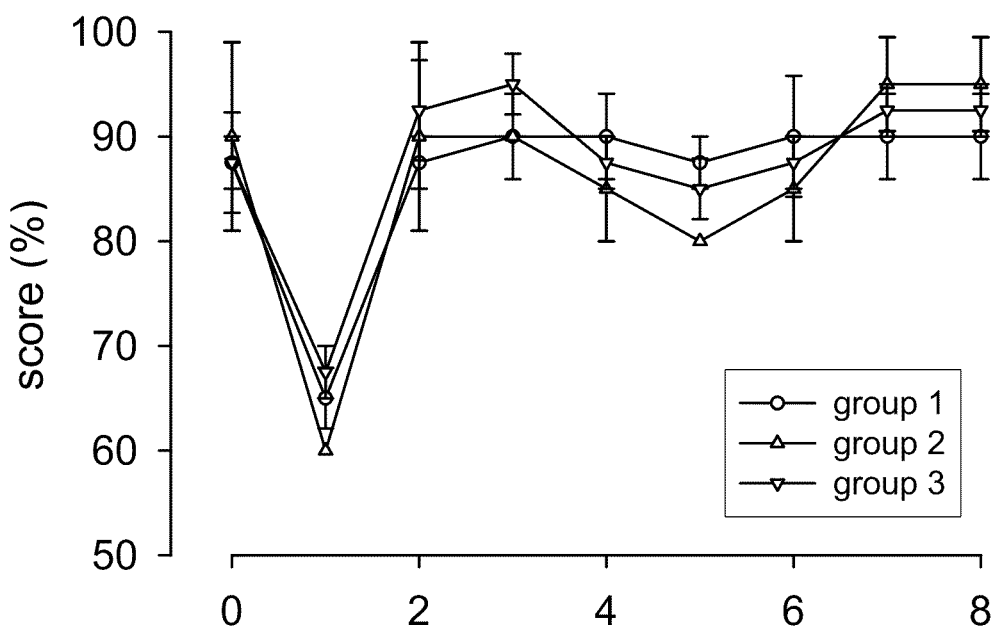
FIG. 3 illustrates that hair cell loss resp. hearing loss induced by acoustic trauma does not play a significant role in the generation of tinnitus. Treatment with D-JNKI-1 prevented hearing loss after acute acoustic trauma, as shown by the rapid recovery of score following trauma (A) but had no significant effect on the prevention of tinnitus, as the prevalence and patterns of tinnitus were essentially the same as in untreated animals (B).
Figure 3:
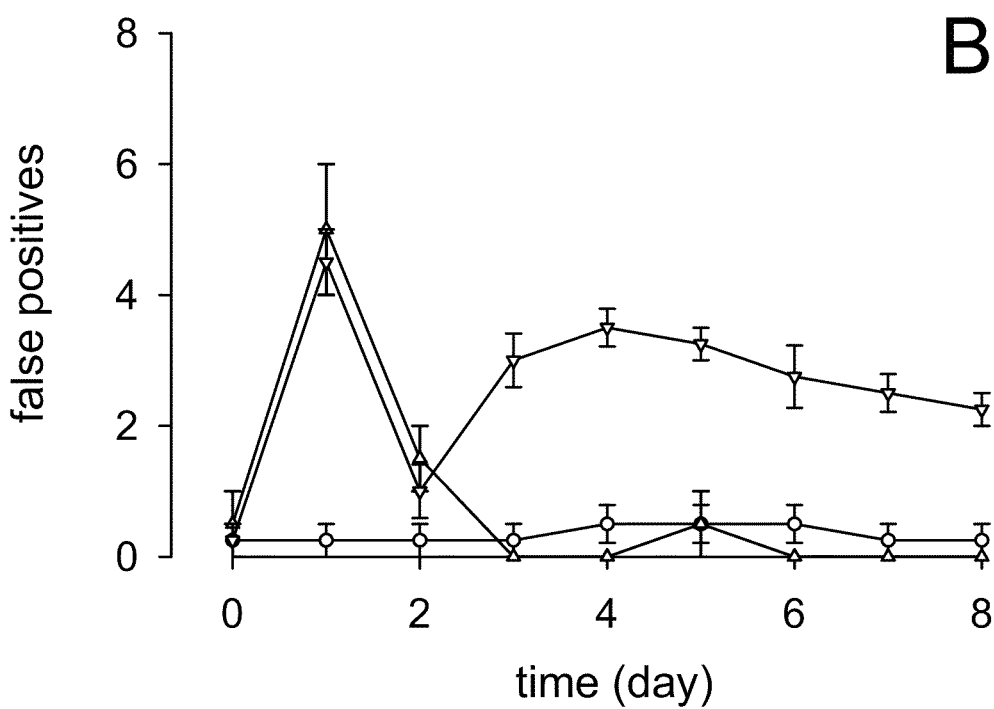

In order to test whether the mechanism underlying the generation of tinnitus by acoustic trauma was linked to the loss of cochlear hair cells and/or to the induction of excitotoxicity, D-JNKI-1 was applied locally to the round window membrane. As shown in FIG. 3A, the pharmaceutical compound could not prevent the decrease of score from day 0 (88%±2.5) to day 1 (65%±1.7). However, treatment resulted in rapid, full functional recovery to pretraumatic levels on day 2 (90%±2.6), which persisted subsequently (92%±2.0 on day 8).

While D-JNKI-1 prevented permanent hearing loss after acute acoustic trauma, it had no significant effect on the number of false positives and thus the prevention of tinnitus. As FIG. 3B shows, the patterns of false positives are almost identical to the ones observed with the control group (FIG. 2B): while group 1 (n=4) showed no increase at all (0.25±0.25 false positives on both days), the two other groups showed again a statistically significant increase (p<0.05) in the number of false positives from day 0 (0.33±0.21) to day 1 (4.66±0.42). As for group 2 (n=2), the increase was again a short-term, fully reversible increase, while the transitory increase in group 3 (n=4) was again followed by a permanent rise in the number of false positives (3.50±0.29 false positives on day 4 and 2.25±0.25 on day 8). Overall, these results suggest that hair cell loss induced by acoustic trauma does not play a significant role in the generation of tinnitus, and point to cochlear excitotoxicity as the mechanism at its base.

Figure 4:
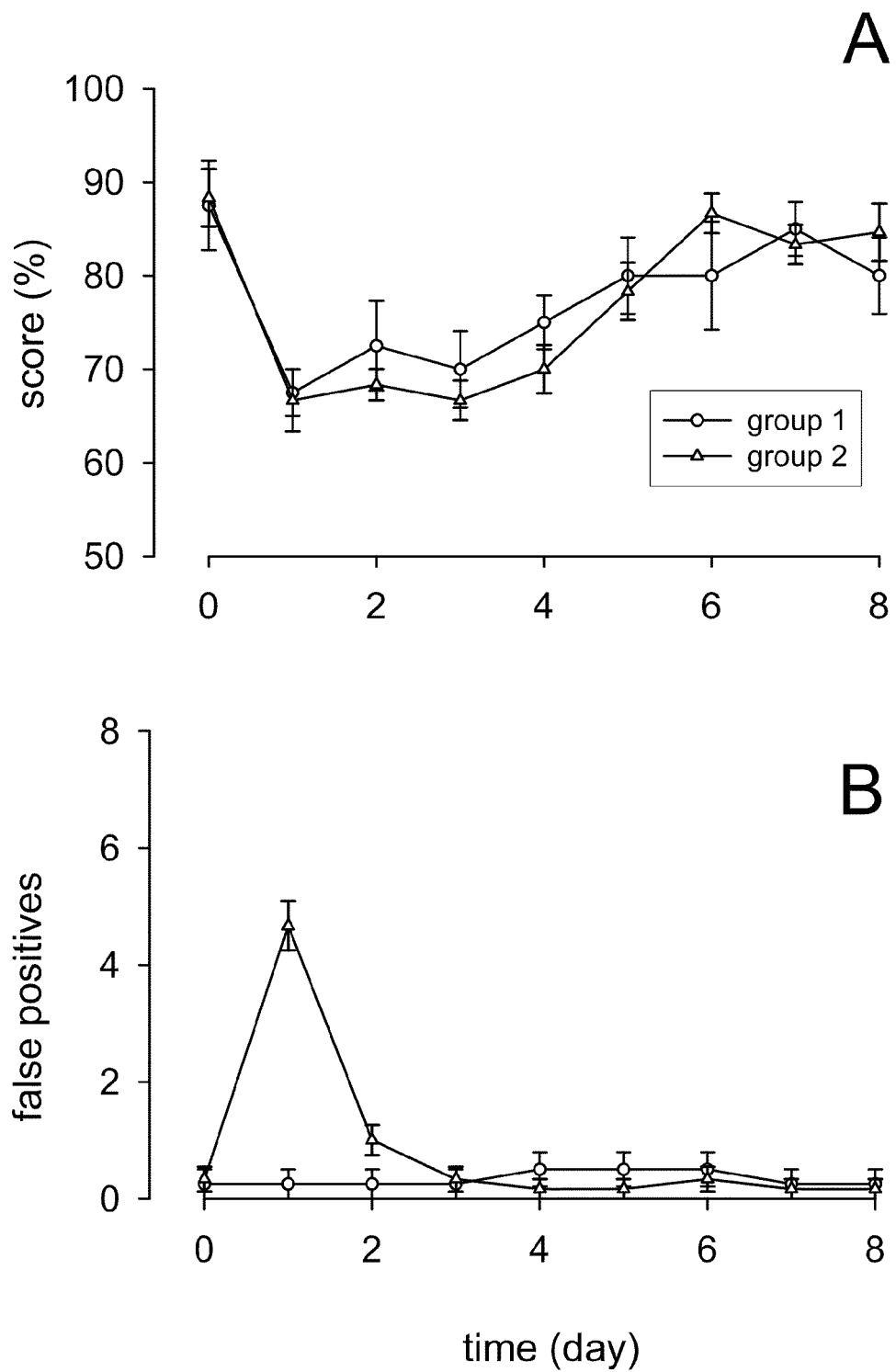
FIG. 4. illustrates that local administration of the NMDA antagonist 7-CK to the round window membrane resulted in the prevention of tinnitus. (A) The average behavioral score dropped from day 0 to day 1 and recovered subsequently; however improvement was slower than in untreated animals. (B) Local administration of the NMDA antagonist 7-CK resulted in suppressing persistent tinnitus induced by cochlear excitotoxicity; only cases of transient tinnitus could be observed.
Figure 5:
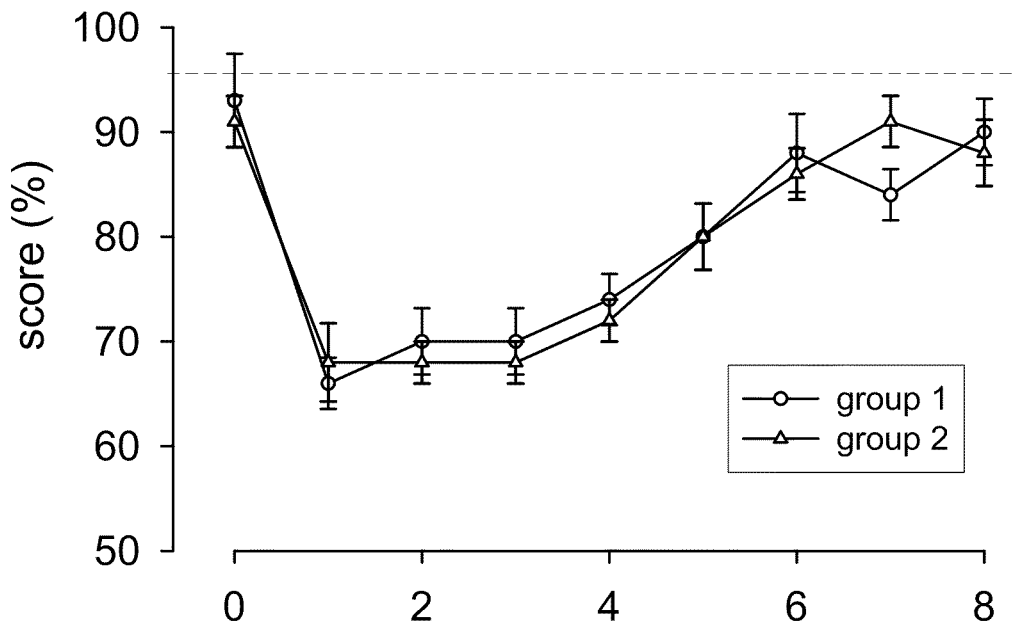
FIG. 5 illustrates that local administration of the NMDA antagonist S-(+)-Ketamine to the round window membrane resulted in the prevention of persistent tinnitus. (A) The average behavioral score dropped from day 0 to day 1 and recovered subsequently; however improvement was slower than in untreated animals. (B) Local administration of the NMDA antagonist S-(+)-Ketamine resulted in suppressing persistent tinnitus induced by cochlear excitotoxicity, only cases of transient tinnitus could be observed.
Figure 5:
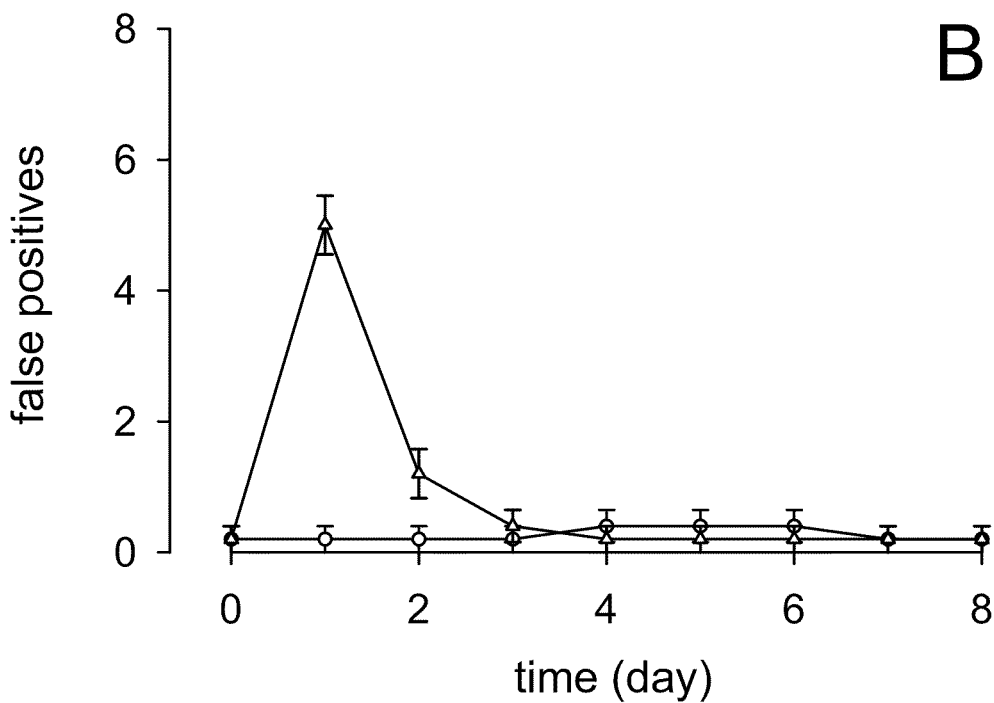

Local application of the two NMDA receptor antagonists 7-CK and S-(+)-Ketamine yielded results, which were very similar to each other. As shown in FIGS. 4A and 5A, the average score dropped significantly from day 0 to day 1 and then recovered, however at a slower rate than in untreated animals. In contrast to untreated animals, the stabilization of the score occurred in the groups of animals treated with NMDA receptor antagonists only on day 6 (89%±2.3 and 88%±2.5, for animals treated with S-(+)-Ketamine and 7-CK, respectively). A possible explanation for this difference may be that the (partial) blocking of NMDA receptors is delaying neosynaptogenesis, where they have a neurotrophic effect, and thus retarding functional recovery.

Administration of the two NMDA antagonists had on the other hand a substantial impact on the number of false positives (FIGS. 4B and 5B). Unlike the untreated animals or those treated with D-JNKI-1, there could be no group observed, where a permanent increase in the number of false positive responses occurred after an initial transitory increase. There was either no increase in false positives at all (group 1; n=5 and n=4 for animals treated with S-(+)-Ketamine and 7-CK, respectively), where false positives of 0.22±0.22 were observed on days 0 and 1, or just the reversible increase right after the acoustic trauma (group 2; n=5 and n=6 for animals treated with ketamine and 7-CK, respectively), with the number of false positives rising from 0.2±0.2 (S-(+)-Ketamine) and 0.33±0.21 (7-CK) on day 0 to 5±0.48 (S-(+)-Ketamine) and 4.66±0.42 (7-CK) on day 1. There were thus no observations of the onset of a persistent tinnitus following the incidence of transitory tinnitus. These results demonstrate that the local administration of NMDA receptor antagonists to the cochlea suppresses persisting tinnitus induced by cochlear excitotoxicity.

Example 2

Methods and Materials

To evaluate the different mechanisms of salicylate and excitotoxicity induced tinnitus, comparative morphological analysis of the cochlear sensorineural structures as well as Western blot immunodetection following the two different types of tinnitus inducing incidents were performed.

Morphology

Two groups of 3 Long Evans rats each were either treated twice a day with an intraperitoneal injection of 350 mg/kg of sodium salicylate for 2 days or traumatized as described. After decapitation of the rats under deep anaesthesia (pentobarbital 50 mg/kg), the cochleas were removed from the temporal bone and perfused with a fixative solution of 2.5% glutaraldehyde in 0.1 M phosphate-buffered saline (PBS), pH 7.3. They were then processed either for scanning (SEM) or transmission electron (TEM) microscopy. For SEM, the otic capsule was dissected out and the stria vascularis, tectorial, and Reissner's membranes were removed. After rinsing in PBS (pH 7.3) the samples were dehydrated in a graded series of ethanol (30-100%), critical point-dried in $CO_2$, coated with gold palladium, and examined using a Hitachi S4000 microscope. For TEM, the cochleas were postfixed in a 1% aqueous solution of osmium tetroxide for 2 hours, rinsed in phosphate buffer, dehydrated in a graded series of ethanol (30-100%), and embedded in Epon resin. Transverse ultrathin sections of the organ of Corti were taken from the apical half of the cochlea. The sections, mounted on formvar-coated or mesh grids, were stained with uranyl acetate, and lead citrate and examined using a Hitachi 7100 microscope.

Immunodetection

Three groups of 3 Long Evans rats each were either treated twice over 24 hours with an intraperitoneal injection of 350 mg/kg of sodium salicylate or traumatized as described in.

The salicylate dose used is known to induce tinnitus (Guitton et al., *J. of Neuroscience* 23 (9): 3944-3952 (2003)). Another group of 3 animals served as control and was injected i.p. with a NaCl 0.9% solution of the same volume as salicylate treated animals. Samples were obtained after 24 hours in the salicylate and control groups and 24 hours respectively 5 days post incident for the acoustic trauma group. As had been shown in Experiment 1, transitory tinnitus occurred 24 hours after the trauma, and persisting tinnitus could be observed from the third day on; therefore it can be expected that persisting tinnitus is present at day 5. Because salicylate cannot induce persisting tinnitus, any treatment and measurement beyond 24 hours cannot be expected to yield results different from those after 24 hours.

Tissues were harvested in cold PBS and homogenized in sample buffer, and the lysates were centrifuged to remove detergent-insoluble material and separated on a 10% SDS-PAGE in Tris/Tricine. After gel electrophoresis, proteins were transferred electrophoretically to nitrocellulose membranes (PVDF transfer membrane Hybond-P, Amersham Pharmacia Biotech, USA). Blots were first incubated with a primary anti-antibody against the NMDA NR1 receptor subunit (1/1000 dilution; rabbit polyclonal antibody, Chemicon international, USA), and with a primary antibody anti-actin (1/50000 dilution, mouse monoclonal anti-β-actin, Sigma, USA) overnight at 4° C. To verify that the molecular weight of the NR1 subunit is identical in both brain and cochlea, immunoblots from the brain of control animals were performed. Then, incubation at 4° C. during 2 hours was done using antibodies anti-rabbit IgG, biotinylated species-specific whole antibody (1/3500, Amersham Lifescience, USA) and anti-mouse IgG, biotinylated species-specific whole antibody (1/3500, Amersham Lifescience, USA). After 5×10 min washes with TBS-T (Tris buffer saline tween), incubation at 4° C. during 2 hours was done using streptavidin alkalin phosphatase conjugate (1/5000, Amersham Lifescience, USA). Protein-antibody complexes were revealed with BCIP/NBT (Sigma, USA). Image scanning of Western blots was then performed for semi-quantification of expression levels of NR1 and actin proteins using Biorad Fluor-S software (Quantity one).

Results

Figure 6:
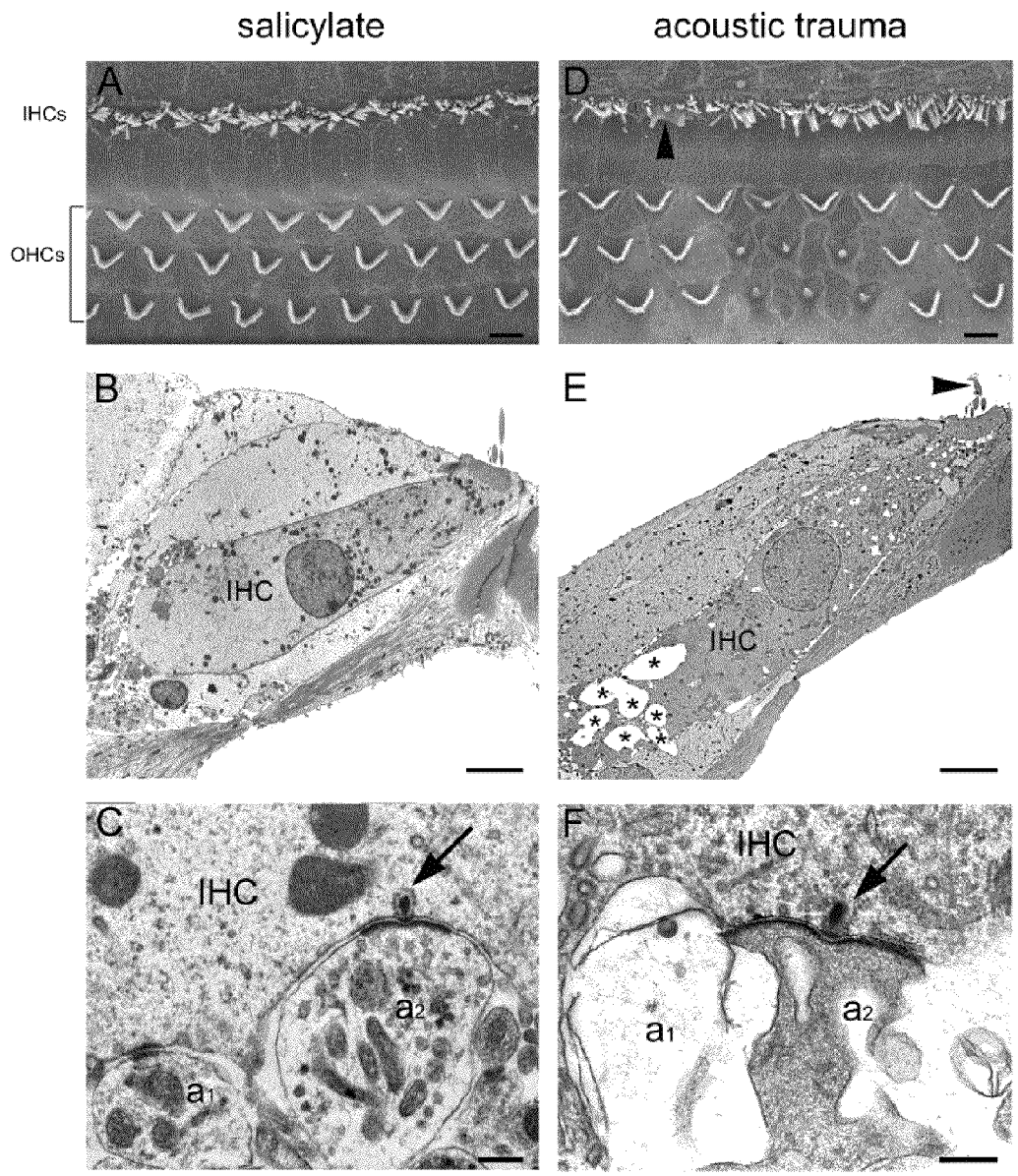
FIG. 6 illustrates that acoustic trauma produces substantial morphological damage on the sensory outer hair cells (OHC) and inner hair cell (IHC) synaptic complex, whereas administration of salicylate does not. The stereocilia of OHC and IHC remain intact following salicylate injections over 2 days (6 A), while those animals which were exposed to acoustic trauma display severe damage to OHC stereociliary bundles as well as disarrayed and in some cases even fused (indicated by black arrowhead) IHC stereocilia (6 D). Low magnification of the IHC synaptic complex shows no ultrastructural abnormalities in case of the salicylate treatment (6 B), whereas in traumatized animals a massive and dramatic swelling (indicated by asterisks) of the radial afferent dendrites can be seen at the basal pole of the IHC in the affected frequency range area, confirming that excitotoxicity has occurred (6E). Note the presence of numerous vacuoles in the apical part of the IHC and abnormally shaped stereocilia (indicated by arrowhead). High magnification of the basal IHC pole shows again no anomalies for the salicylate treated animal (6 C). The two afferent nerve endings (indicated by a1 and a2) are normal, and a characteristic presynaptic body facing afferent a2 is clearly visible. Contrary to this, (6 F) displays swollen (a1)) and disrupted (a2) nerve endings and the presynaptic body facing a2. Scale bars for A and D are 10 µm (scanning electron microscopy), for B and E 5 µm, and for C and F 0.25 µm (all transmission electron microscopy).

As expected, the mechanisms underlying salicylate and excitotoxicity induced tinnitus imply different pathways and result in different morphological and physiological outcomes. As shown in FIG. 6, administration of salicylate leaves the stereocilia of sensory outer hair cells (OHC) and inner hair cells (IHC) intact, while those animals which were exposed to acoustic trauma display severe damage to OHC stereociliary bundles as well as disarrayed and in some cases even fused IHC stereocilia. No ultrastructural abnormalities of the IHC synaptic complex can be seen in case of the salicylate treatment, whereas in traumatized animals a massive and dramatic swelling of the radial afferent dendrites is evident at the basal pole of the IHC in the affected frequency range area, confirming that excitotoxicity has occurred. Numerous vacuoles in the apical part of the IHC and abnormally shaped stereocilia are present. High magnification of the basal IHC pole shows again no anomalies for the salicylate treated animal. The afferent nerve endings are normal, and a characteristic presynaptic body is clearly visible. Contrary to this, following trauma, swollen and disrupted nerve endings appear.

Figure 7:
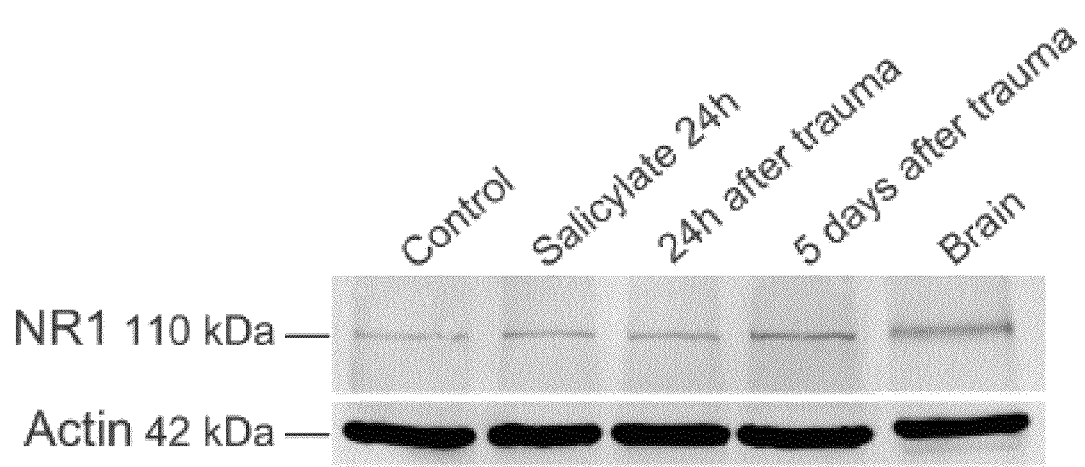
FIG. 7 illustrates the expression of the NR1 subunit of the cochlear NMDA receptor following exposure to salicylate or acoustic trauma, determined by Western Blot immunodetection. As can be seen, the salicylate treatment did not induce any significant modification of NR1 NMDA receptor subunit expression (4% higher than control animals). In contrast, acoustic trauma led to a clear overexpression 5 days after the incident (+50% over control animals), which is consistent with the observation of persisting tinnitus. However, 24 hours post trauma, there is no significant overexpression detectable (+8%), which suggests that the mechanisms of transitory and permanent tinnitus after acoustic trauma are fundamentally different. Immunoblots from the brain of control animals were performed to verify that the molecular weight of the NR1 subunit is identical in both brain and cochlea.

FIG. 7 shows the expression of the NR1 subunit of the cochlear NMDA receptor following exposure to salicylate or acoustic trauma, determined by Western Blot immunodetection. The salicylate treatment did not induce any significant modification of NR1 NMDA receptor subunit expression (4% higher than control animals). In contrast, acoustic trauma led to a clear overexpression 5 days after the incident (+50% over control animals), which is consistent with the observation of persisting tinnitus. The difference in NMDA NR1 expression shows that tinnitus induced by acoustic trauma is up-regulating NMDA receptors, whereas salicylate does not. This confirms that salicylate induced tinnitus is mediated by a different pathway, as discussed above. FIG. 7 shows further that 24 hours post trauma, there is no overexpression detectable (+8%), which suggests that the mechanisms of transitory and permanent tinnitus after acoustic trauma are fundamentally different.

Taken together, the results of the morphological and immunodetection analysis confirm the suggested fundamental difference in mechanisms of action between salicylate and excitotoxicity induced tinnitus. Excitotoxicity does, unlike salicylate, damage the inner hair cell synaptic complex and induce an upregulation of NMDA receptors, leading in turn to the occurrence of persisting tinnitus. As two different pathways in the regulation of cochlear NMDA responses are involved, efficacy of NMDA receptor antagonists in suppressing persisting tinnitus induced by cochlear excitotoxicity could realistically not be presumed by a model of salicylate induced tinnitus.

Example 3

Methods and Materials

In order to confirm and extend the results obtained in the previous experiments, we developed and tested another animal model of tinnitus induced by cochlear excitotoxicity, which allowed direct measurement of the presence of tinnitus, i.e. without using a behavioural model. Martin et al., *Proceedings of the Fifth International Tinnitus Seminar, American Tinnitus Association:* 127-134 (1996) described a narrow spectral peak at approximately 200 Hz in the spectrum of the ensemble spontaneous activity ("ESA") of the cochlear nerve in persons suffering from tinnitus. These results were consistent with findings in various animal models of from tinnitus. These results were consistent with findings in various animal models of tinnitus, suggesting that this peak was indeed an objective correlate of tinnitus. There has been, however, no specific objective evaluation of tinnitus induced by cochlear excitotoxicity, neither in human beings, nor in animals.

We developed therefore an animal model with guinea pigs that were exposed to intensive noise, producing acute acoustic trauma, and whose ESA was recorded to control for the absence or presence of tinnitus ("ESA noise trauma model"). The possibility to record tinnitus by electrophysiological tests provides an excellent tool for evaluating the therapeutic benefits of pharmaceutical compounds in suppressing tinnitus. The development of the ESA noise trauma model required extensive experimentation with different noise trauma protocols as well as the development and testing of specific measurement tools for extended observation periods in vivo.

The experiment was performed in two stages. First, guinea pigs were exposed to intense noise stimulation in order to provoke acute acoustic trauma (day 0). Auditory thresholds and ESA were determined and then followed further by repeated electrophysiological measurements. If persisting tinnitus could still be detected after at least 5 days, an NMDA receptor antagonists (ketamine or 7-CK) was applied in a hyaluronic acid formulation onto the round window membrane of the cochlea. The waiting period was observed to ensure that no cases of transitory, short-term tinnitus were included; in addition, we were seeking to extend the observation period used in Example 1. After treatment with the NMDA receptor antagonists, electrophysiological measurements of hearing thresholds and ESA continued for at least 10 days. The primary endpoints of the study were to test whether the pharmacological treatment could suppress tinnitus even after its onset, and whether such treatment effect was persisting or not. As a control, contralateral ears were exposed to the same noise exposure and followed by electrophysiology.

Animals

Experiments were performed on adult pigmented guinea pigs (250 to 300 grams at study begin). During experiments, animals were caged individually. Outside the experiments, the animals received water and nutrition ad libidum. A total of 8 animals were tested in stage 1, of which 3 animals showed persisting and stable tinnitus in their right ear for at least 10 days (minimum 10 days, maximum 30 days), as measured by ESA, and were subsequently treated by one of the two NMDA receptor antagonists. In two contralateral left ears, tinnitus was observed, so that they could be used as a control group.

Acoustic Trauma

Acoustic trauma was induced by a continuous pure tone of 6 kHz generated by a waveform synthesizer (Hewlett-Packard 8904A). The animals were anesthetized and exposed to 130 dB sound pressure level (SPL) for 15 to 40 minutes, which was routed through a programmable attenuator and presented to the ears in free field via a JBL 075 earphone positioned 10 cm laterally to the animal's ear. Sound level was measured using a calibrated Bruel and Kjaer microphone (4314) and a Bruel and Kjaer calibrating amplifier (2606).

Electrophysiology

A teflon-coated platinum electrode implanted onto the round window membranes of both cochleas (with reference electrodes placed in a neck muscle) measured the ESA and the compound action potential of the auditory nerve (CAP). The surgery was performed using a posterior auricular surgical procedure (dorsal approach) prior to noise exposure. The reference electrode and the round window electrode were soldered to a plug fixed on the skull using dental cement (Unifast Trad, GC Corporation).

The ESA was recorded from the platinum wire placed in the round window niche. The signal was amplified by a DC powered amplifier (Radio Spare VIP 20) and A to D converted (48 kHz sampling frequency) by a 24 bits converter (National Instrument 4474, USA). Spectral analysis of the signal was performed with the customized computer software LabVIEW 7.1 (200 averages, Hanning window, 0-3125 kHz) and the power spectrum was displayed as a function of frequency on a PC computer (Dell Dimension).

The CAP was measured concomitantly with ESA measurements using the same electrode. Tone bursts (with a duration of 9 ms and a rise/fall cycle of 1 ms, 10 per second) generated by an arbitrary function generator (LeCroy Corp., model 9100R) were applied to the animal's ear in free filed via a JBL 075 earphone. CAP audiograms were obtained by varying burst levels from 0 to 100 dB SPL in steps of 5 dB at the frequencies 2, 4, 6, 8, 10, 12, 16, 20, and 26 kHz. Auditory nerve responses were amplified (Tektronic™ 503; gain 2000), filtered (3.5 kHz low pass) and averaged on a PC (Dimension Pentium, Dell). CAP amplitudes were measured peak-to-peak between the first negative depression N1 and the subsequent positive wave P1. The CAP threshold was defined as the sound intensity (in dB SPL) needed to elicit a measurable response (greater than 5 µV).

Protocol

The ESA was measured just before acute acoustic trauma and 20 minutes following noise exposure on day 0, and then repeatedly for at least 10 days as described above. Upon the last ESA measurement confirming the presence of persisting and stable tinnitus, the animals received the NMDA receptor antagonist treatment onto the round window membrane of the cochlea (treatment day T). Subsequently, ESA was measured again on the first day after treatment (T+1) as well as 10 days after treatment (T+10).

Pharmacology

On treatment day (T), the animals were anaesthetized with a single-dose s.c. (subcutaneous) injection of Zoletil 50 (Virbac, France)-Rompun 2% (Bayer, Germany) at 55 µl/100 grams and operated under aseptic conditions. The right bullae were re-opened through a posterior auricular surgical procedure (lateral dorsal approach) with particular care being applied in order not to displace the recording electrode. After exposure of the cochlea, 100 microliters of a gel formulation (0.7% hyaluronic acid, Hylumed Sterile, Genzyme Corp., with phosphate buffer), with either S-(+)-Ketamine (Sigma-Aldrich) or 7-CK (Sigma-Aldrich) at a concentration of 50 microM were deposited in the bulla. The bulla was then closed with dental cement (Unifast Trad, GC Corporation), the wounds disinfected and sutured. 2 animals received Ketamine and 1 animal received 7-CK.

Results

Experimentation with various durations showed that noise exposure during 40 minutes produced stable and persisting tinnitus. All treated animals were subjected therefore to a protocol with 130 dB of noise at 6 kHz for 40 minutes. This intensive noise exposure resulted in substantial temporary threshold shifts and permanent hearing loss (mean permanent threshold shift) of at least 40 dB.

Figure 8:
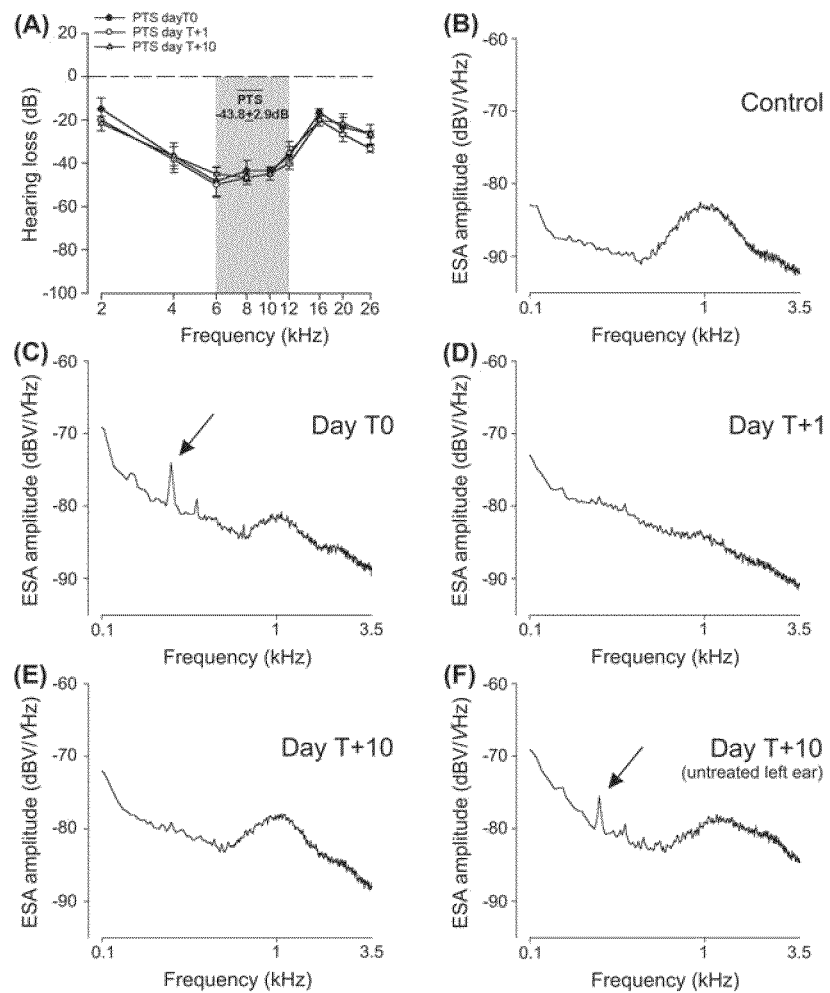
FIG. 8 shows the ensemble spontaneous activity (ESA) of the cochlear nerve in guinea pigs following cochlear excitotoxicity which induces tinnitus and the effects of a subsequent treatment by an NMDA antagonist. (A) shows the permanent threshold shift (PTS) of the auditory function resulting from the exposure to noise at the beginning of the experiment. (B) shows the ESA recording just prior to the exposure of the animal to 130 dB of sound at 6 kHz during 40 minutes. Note the spectral peak centered at around 900 Hz to 1 kHz which is indicative of a normal hearing activity. (C) shows the ESA recording 5 days after the noise exposure on T0. Note the spectral peak in the 200 to 250 frequency range, which is indicative of the presence of tinnitus. This peak had appeared immediately after the noise trauma and persisted from then on in a stable way. The regular spectral peak, however, had disappeared and subsequently recovered. The contralateral ear showed exactly the same pattern of ESA with a peak at 200 to 250 Hz, indicating also the presence of tinnitus. Following these measurements, the animal was treated on T0 with the NMDA antagonist Ketamine by local administration onto the round window membrane. (D) On the day following treatment administration (T1), the ESA recording for the treated ear showed the absence of the 200 to 250 Hz spectral peak, indicating the successful suppression of tinnitus. The regular peak centered at 900 Hz to 1 kHz still appeared, yet diminished. In the contralateral ear, tinnitus was still measured. (E) 10 days after treatment (T+10) the spectral peak at 200 to 250 Hz still remained absent, demonstrating a lasting effect of the treatment. In addition, the regular peak centered at around 900 Hz to 1 kHz had fully recovered. (F) In the untreated left ear, the presence of tinnitus was still indicated by the ESA recording. Please note that the PTS was not changed by the treatment (A), i.e. hearing remained unaffected, which indicates that the treatment is not only effective, but also does not produce any side effects.

As shown in FIG. 8, the regular spectral peak of ESA centered at 900 Hz to 1 kHz was present prior to the noise exposure. Immediately following the noise trauma, the ESA recording showed the emergence of abnormal activity of the cochlear nerve with a spectral peak centered at 200 to 250 Hz, which persisted and remained stable thereafter. Contrary to this, the regular spectral peak centered at 900 Hz to 1 kHz, which represents the ensemble spontaneous activity of the auditory nerve, was significantly reduced and recovered only within 5 days. This evolution is consistent with the occurrence of temporary threshold shift and the following recovery of auditory function.

On the day of administration of the NMDA receptor antagonist, all animals were tested to verify the presence of the spectral peak centered at 200 to 250 Hz in both of their ears. One ear could no longer be tested, as the recording electrode no longer functioned properly. The regular spectral peak centered at 900 Hz to 1 kHz had fully recovered by now, and hearing threshold levels had recovered partially. Animals 1 and 2 received Ketamine and animal 3 received 7-CK, Contralateral ear readings were possible in animals 1 and 2. In all three animals, the ESA peak centered at 200 to 250 Hz completely disappeared on day T1 and remained absent on the follow-up measurement on T10. In the contralateral ears, the peak remained unaffected on T1 and was still well present on T10. Importantly, the hearing loss (permanent threshold shift) observed on day T remained unaffected by the pharmacological treatment of tinnitus. The results shown in FIG. 8 are fully representative of the results obtained with the other animals, i.e. the very same observations were made.

The present results confirm those obtained in the previous experiments and show that the local administration of NMDA receptor antagonists is very effective in suppressing tinnitus induced by cochlear excitotoxicity. It is important to note that the conditions of the experiment are very close to real life conditions with regard to the patterns of hearing loss following acute acoustic trauma and the possibility to treat tinnitus only after its onset. The present results clearly show for the first time ever that the tested pharmaceutical compounds are not only effective when administered preventively, i.e. before the onset of tinnitus, but also afterwards, and that the therapeutic window is not limited to just a few hours or days. This finding is very important in view of frequent failures of NMDA receptor antagonists in clinical trials for the treatment of stroke, which had previously shown excellent efficacy in animals when applied prior to the incident or shortly thereafter (see e.g. Stroke Therapy Academic Industry Roundtable, *Stroke* (30): 2752-2758 (1999)).

The invention claimed is:

1. A method for treating tinnitus induced by cochlear excitotoxicity in a human, the method comprising administering to a human a therapeutically effective amount of a pharmaceutical composition comprising an NMDA receptor antagonist ketamine, effective to suppress or reduce NMDA receptor mediated aberrant activity of the auditory nerve in a human in need of such treatment.

2. A method for treating tinnitus induced by cochlear excitotoxicity in a human, the method comprising administering to a human a therapeutically effective amount of a pharmaceutical composition comprising an NMDA receptor antagonist ketamine, effective to treat NMDA receptor mediated aberrant activity of the auditory nerve in a human in need of such treatment.

3. The method of claim 1, wherein the cochlear excitotoxicity is provoked by an occurrence selected from the group consisting of acoustic trauma, presbycusis, ischemia, anoxia, treatment with one or more ototoxic medications, and sudden deafness.

4. The method of claim 1, wherein the pharmaceutical composition is administered topically via the round window membrane or the oval window membrane to the inner ear.

5. The method of claim 1, wherein the pharmaceutical composition is administered topically by means of invasive drug delivery techniques to the inner ear.

6. The method of claim 3, wherein the cochlear excitotoxicity is characterized as acute.

7. The method of claim 3, wherein the cochlear excitotoxicity is characterized as repeated.

8. The method of claim 3, wherein the cochlear excitotoxicity is characterized as prolonged or chronic.

9. The method of claim 1, wherein the pharmaceutical composition comprises a ketamine analog, a ketamine derivative, a ketamine enantiomer, or pharmaceutically acceptable salt thereof.

10. The method of claim 2, wherein the pharmaceutical composition comprises a ketamine analog, a ketamine derivative or a ketamine enantiomer.

11. The method of claim 1, wherein the ketamine is (S)-ketamine or pharmaceutically acceptable salt thereof.

12. The method of claim 2, wherein the ketamine is (S)-ketamine or pharmaceutically acceptable salt thereof.

13. The method of claim 1, wherein the ketamine is enantiomerically enriched for (S)-ketamine or pharmaceutically acceptable salt thereof.

14. The method of claim 2, wherein the ketamine is enantiomerically enriched for (S)-ketamine or pharmaceutically acceptable salt thereof.

* * * * *